US009962141B2

(12) United States Patent
Kim

(10) Patent No.: US 9,962,141 B2
(45) Date of Patent: May 8, 2018

(54) IMAGE PROCESSING APPARATUS, ULTRASONIC IMAGING APPARATUS, AND IMAGING PROCESSING METHOD FOR IMPROVING IMAGE QUALITY BASED ON CONVERSION RELATING TO VIRTUAL ILLUMINATION POSITION

(71) Applicant: SAMSUNG ELECTRONICS CO., LTD., Suwon-si (KR)

(72) Inventor: Yun Tae Kim, Hwaseong-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 269 days.

(21) Appl. No.: 14/136,128

(22) Filed: Dec. 20, 2013

(65) Prior Publication Data
US 2014/0205168 A1  Jul. 24, 2014

(30) Foreign Application Priority Data
Jan. 23, 2013  (KR) .................. 10-2013-0007494

(51) Int. Cl.
*G06K 9/00* (2006.01)
*A61B 8/00* (2006.01)
(Continued)

(52) U.S. Cl.
CPC ................ *A61B 8/46* (2013.01); *G06T 15/08* (2013.01); *G06T 15/50* (2013.01); *A61B 8/0866* (2013.01); *G06T 2210/41* (2013.01)

(58) Field of Classification Search
CPC . G06T 7/0012; G06T 2210/41; G06T 11/003; G06T 15/08; G06T 15/50; G06T 2207/10152; G06T 2207/30004
See application file for complete search history.

(56) References Cited

U.S. PATENT DOCUMENTS

2004/0263511 A1* 12/2004 West et al. ..................... 345/421
2005/0065425 A1*  3/2005 Matsumoto ................... 600/407
(Continued)

FOREIGN PATENT DOCUMENTS

JP  2006-218210 A   8/2006
JP  2010-221033 A  10/2010
(Continued)

OTHER PUBLICATIONS

Kniss et al., A Model for Volume Lighting and Modeling, 2003, IEEE Transactions on Visualization and Computer Graphics, vol. 9, No. 2, pp. 150-162.*
(Continued)

*Primary Examiner* — Vu Le
*Assistant Examiner* — Guillermo Rivera-Martinez
(74) *Attorney, Agent, or Firm* — Sughrue Mion, PLLC

(57) ABSTRACT

Disclosed herein is an image processing apparatus. The image processing apparatus collects volume data which relates to an object, generates volume-rendered image data from the collected volume data, acquires a projection image of the object at a position at which virtual illumination is emitted toward the object, based on the volume-rendered image data, and corrects the projection image by using at least one conversion function, thereby obtaining a result image.

18 Claims, 17 Drawing Sheets
(4 of 17 Drawing Sheet(s) Filed in Color)

(51) Int. Cl.
*G06T 15/50* (2011.01)
*G06T 15/08* (2011.01)
*A61B 8/08* (2006.01)

(56) References Cited

U.S. PATENT DOCUMENTS

| | | | |
|---|---|---|---|
| 2007/0002047 A1* | 1/2007 | Desgranges et al. | 345/426 |
| 2007/0238957 A1* | 10/2007 | Yared | 600/407 |
| 2009/0006052 A1* | 1/2009 | Zhou et al. | 703/5 |
| 2009/0243916 A1* | 10/2009 | Beeri et al. | 342/179 |
| 2010/0121190 A1* | 5/2010 | Pagoulatos et al. | 600/437 |
| 2010/0142804 A1* | 6/2010 | Mallick et al. | 382/162 |
| 2011/0069069 A1* | 3/2011 | Engel | 345/426 |
| 2011/0109631 A1* | 5/2011 | Kunert et al. | 345/426 |
| 2013/0120656 A1* | 5/2013 | Wilson | G06F 3/1462 348/563 |

FOREIGN PATENT DOCUMENTS

KR 10-0870412 B1 11/2008
KR 10-0873336 B1 12/2008

OTHER PUBLICATIONS

Jain et al., Machine Vision, 1995, McGraw-Hill, Inc., ISBN 0-07-032018-7, pp. 123-133.*

* cited by examiner

IMAGE PROCESSING APPARATUS, ULTRASONIC IMAGING APPARATUS, AND IMAGING PROCESSING METHOD FOR IMPROVING IMAGE QUALITY BASED ON CONVERSION RELATING TO VIRTUAL ILLUMINATION POSITION

CROSS-REFERENCE TO RELATED APPLICATION(S)

This application claims priority from Korean Patent Application No. 10-2013-0007494, filed on Jan. 23, 2013 in the Korean Intellectual Property Office, the disclosure of which is incorporated herein by reference in its entirety.

BACKGROUND

1. Field

Exemplary embodiments relate to an image processing apparatus and method.

2. Description of the Related Art

In modern times, a variety of imaging apparatuses have been used in order to capture images of the exteriors or interiors of objects.

Examples of various imaging apparatuses include a camera, a digital radiography (DR) apparatus, a computed tomography (CT) apparatus, a magnetic resonance imaging (MRI) apparatus, and an ultrasonic imaging apparatus.

These imaging apparatuses collect various data which relate to an object by using visible light, infrared light, radiation such as X-rays, and/or ultrasonic waves, and generate an image by using the collected data.

A user can neither directly interpret nor read data which is collected by such imaging apparatuses, and thus, a process for converting the collected data via a predetermined image processing unit of the imaging apparatuses into an image that can be viewed by a user is generally performed via predetermined image processing.

SUMMARY

Therefore, it is an aspect of one or more exemplary embodiments to provide an image processing apparatus and method that may improve a quality of an image which has been acquired based on collected image data by using at least one conversion function that varies based on a change in the position of virtual illumination, and an ultrasonic imaging apparatus to which the image processing apparatus and method are applied.

Additional aspects of the exemplary embodiments will be set forth in part in the description which follows and, in part, will be apparent from the description, or may be learned by practice of the exemplary embodiments.

To achieve the technical goals, an image processing method, an image processing apparatus, and an ultrasonic imaging are provided.

In accordance with one aspect of one or more exemplary embodiments, an image processing method includes acquiring, by an image processing apparatus, volume-rendered image data by using volume data which relate to an object and correcting the acquired image data by using at least one conversion function which is determined based on a virtual illumination position which relates to the object. In this regard, the virtual illumination position indicates a position at which a virtual illumination unit emits virtual illumination toward the object.

The correcting may include adjusting a brightness of the acquired image data by using a first conversion function which is determined based on coordinates of the virtual illumination position, performing a tone mapping by using a second conversion function, and/or performing a hue correction by using a third conversion function.

The first conversion function may include a function which is expressible by Equation 1 below:

$$l(\phi, \theta) = 1 - Ae^{-\left(\frac{(\phi-\phi_0)^2}{2\sigma_\phi^2} + \frac{(\theta-\theta_0)^2}{2\sigma_\theta^2}\right)} \quad \text{[Equation 1]}$$

wherein $(\phi,\theta)$ denotes respective coordinates of the virtual illumination position in a spherical coordinate system, $(\phi_0,\theta_0)$ denotes respective coordinates of a reference position in the spherical coordinate system, $\sigma_\phi$ and $\sigma_\theta$ denote respective values which relate to a distribution of a first virtual illumination position, and A denotes a predetermined constant.

The second conversion function may include a function which is expressible by Equation 2 below:

$$p(x, \phi, \theta) = \frac{1}{1 + \alpha \cdot e^{-\beta(\phi,\theta)x}} \quad \text{[Equation 2]}$$

wherein x denotes an image value of a respective voxel, $\phi$ and $\theta$ denote respective coordinates of the virtual illumination position in a spherical coordinate system, $\alpha$ denotes a predetermined constant, and $\beta(\phi,\theta)$ denotes a value which is determined based on the virtual illumination position. In this case, $\beta(\phi,\theta)$ may be determined by applying Equation 3 below.

$$\beta(\phi, \theta) = Ae^{-\left(\frac{(\phi-\phi_0)^2}{2\sigma_\phi^2} + \frac{(\theta-\theta_0)^2}{2\sigma_\theta^2}\right)} \quad \text{[Equation 3]}$$

wherein $(\phi_0,\theta_0)$ denotes respective coordinates of a reference position in the spherical coordinate system, $\sigma_\phi$ and $\sigma_\theta$ denote respective values which relate to a distribution of a first virtual illumination position, and A denotes a predetermined constant.

The third conversion function may include a function which is expressible by Equation 4 below:

$$C(x,s,\phi,\theta) = x \cdot s \cdot [(1-\epsilon) + \epsilon \cdot l(\phi,\theta)] \quad \text{[Equation 4]}$$

wherein x denotes an image value of a respective voxel, s denotes a shadow value, $\phi$ and $\theta$ denote respective coordinates of the virtual illumination position in a spherical coordinate system, $\epsilon$ denotes a luminance attenuation constant, and $l(\phi,\theta)$ denotes a luminance attenuation value which relates to the virtual illumination position.

In accordance with another aspect of one or more exemplary embodiments, an image processing apparatus includes a volume data collector which is configured to collect volume data which relate to an object and an image processor which is configured to acquire rendered image data by performing volume rendering with respect to the collected volume data and to correct the collected image data by using at least one conversion function which is determined based on a virtual illumination position which relates to the object. In this regard, the at least one conversion function may include at least one of the first, second and third conversion functions.

In accordance with another aspect of one or more exemplary embodiments, an ultrasonic imaging apparatus includes an ultrasonic probe which is configured to transmit ultrasonic waves to an object and to receive ultrasonic echo waves which are reflected from the object, a beamformer which is configured to perform beamforming based on the ultrasonic echo waves which are received by the ultrasonic probe, a volume data generator which is configured to acquire volume data which relate to the object based on the resulting beamformed data, and an image processor which is configured to acquire image data by performing volume rendering with respect to the volume data and to correct the acquired image data by using at least one conversion function which is determined based on a virtual illumination position which relates to the object. In this regard, the at least one conversion function may include at least one of the first, second and third conversion functions.

BRIEF DESCRIPTION OF THE DRAWINGS

The patent or application file contains at least one drawing executed in color. Copies of this patent or patent application publication with color drawing(s) will be provided by the Office upon request and payment of the necessary fee. The foregoing and/or other aspects will become apparent and more readily appreciated from the following description of the exemplary embodiments, taken in conjunction with the accompanying drawings of which.

DETAILED DESCRIPTION

Figure 1:
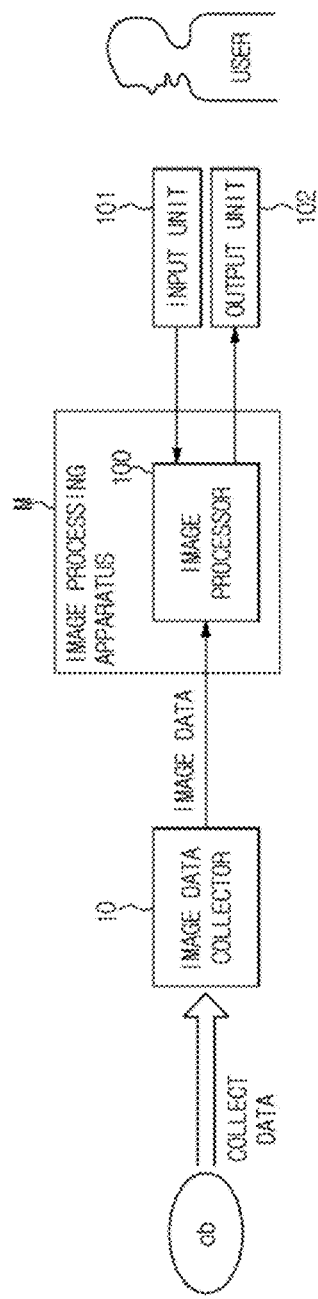
FIG. 1 is a block diagram which illustrates a configuration of an image processing apparatus, according to an exemplary embodiment.

Reference will now be made in detail to exemplary embodiments, examples of which are illustrated in the accompanying drawings, wherein like reference numerals refer to like elements throughout.

FIG. 1 is a block diagram which illustrates a configuration of an image processing apparatus M, according to an exemplary embodiment.

As illustrated in FIG. 1, the image processing apparatus M includes an image data collector 10 which is configured to collect image data which is used to generate an image of an object ob and an image processor 100 which is configured to generate a result image by performing predetermined image processing on the image data collected by the image data collector 10.

The image data collector 10 collects raw image data from the object ob. In this regard, the raw image data may include volume data that provides a three-dimensional representation of the object ob.

The image data collector 10 may include, for example, an ultrasonic probe that transmits ultrasonic waves to the object ob and receives an ultrasonic echo signal which is reflected from the object ob in an imaging apparatus m according to an exemplary embodiment, i.e., an ultrasonic imaging apparatus. In a case in which the image processing apparatus m is applied to a CT apparatus, the image data collector 10 may include a radiation emission module which is configured to irradiate an object with radiation such as X-rays, a radiation detection module which is configured to detect radiation which has propagated through the object or radiation which directly reaches the radiation detection module without having passed through the object, and the like. When a magnetic resonance imaging apparatus is used as the image processing apparatus m, the image data collector 10 may include a high frequency coil which is configured to apply electromagnetic waves to an object which is exposed to a static magnetic field and a gradient magnetic field and to receive a magnetic resonance signal which is generated due to a magnetic resonance phenomenon of atomic nuclei inside the object in response to the applied electromagnetic waves, and the related devices.

The image processor 100 performs rendering based on image data which relate to the object and are collected by the image data collector 10, corrects the rendered image data in order to generate a final image, and transmits the corrected image data to an output unit 102 which is installed in an external workstation which is connected to the image processing apparatus M via a wired or wireless communication network or installed in the image processing apparatus M, the output unit 102 including, e.g., a device which includes a display unit such as a smart phone, a monitor, or the like, or an image forming apparatus such as a printer so that a user can check the resultant corrected image.

In this case, the image processor 100 may be connected to the image processing apparatus M via a wired or wireless communication network, or receive predetermined commands or instructions from a user via an input unit 101 which is installed in the image processing apparatus M. The image processor 100 may be configured to initiate rendering or image correction based on the predetermined commands or instructions which are input via the input unit 101, or to generate or revise various settings which may be needed for rendering or image correction and then perform rendering or image correction based on the generated or revised settings. In this regard, the input unit 101 may include any one or more of various members that enable a user to input data, instructions, or commands, such as, e.g., a keyboard, a mouse, a trackball, a tablet, a touch screen, and/or the like.

When the image data includes volume data which relates to the object ob, the image processor 100 may acquire a projection image of the object ob which corresponds to one or more view points of a user. In addition, the image processor 100 corrects the image data collected by the image data collector 10 based on a position of virtual illumination which is emitted toward the object ob and rendered in order to acquire a result image. In this case, the view points of a user and/or the position of virtual illumination may be input via the input unit 101.

Figure 2:
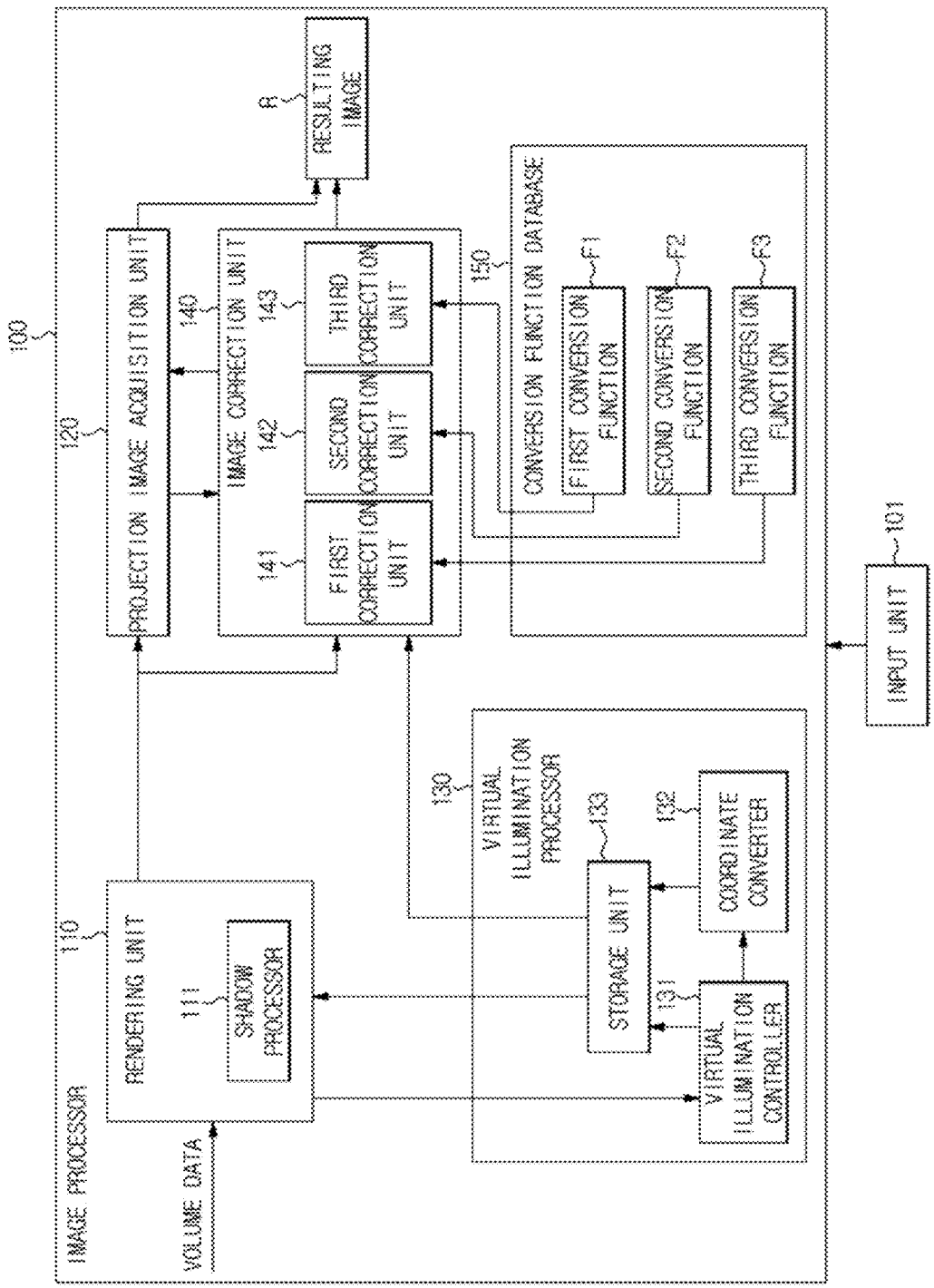
FIG. 2 is a block diagram of an image processor of the image processing apparatus, according to an exemplary embodiment.

FIG. 2 is a block diagram which illustrates the imaging processor 100, according to an exemplary embodiment.

As illustrated in FIG. 2, the imaging processor 100 may include a rendering unit 110 (also referred to herein as a renderer 110), a projection image acquisition unit 120 (also referred to herein as a projection image acquirer 120), a virtual illumination processor 130, and an image correction unit 140 (also referred to herein as an image corrector 140).

The rendering unit 110 performs rendering based on image data which is collected and which relate to the object ob. In particular, the collected image data are mixed to reconstruct a 2D or 3D image of the object ob. When the image data collected by the image data collector 10 are volume data which are represented by a plurality of voxels, the rendering unit 110 performs volume rendering upon the collected volume data of the object ob in order to reconstruct image data into a 3D visual image. Accordingly, a 3D image of the object ob is acquired.

Figure 3:
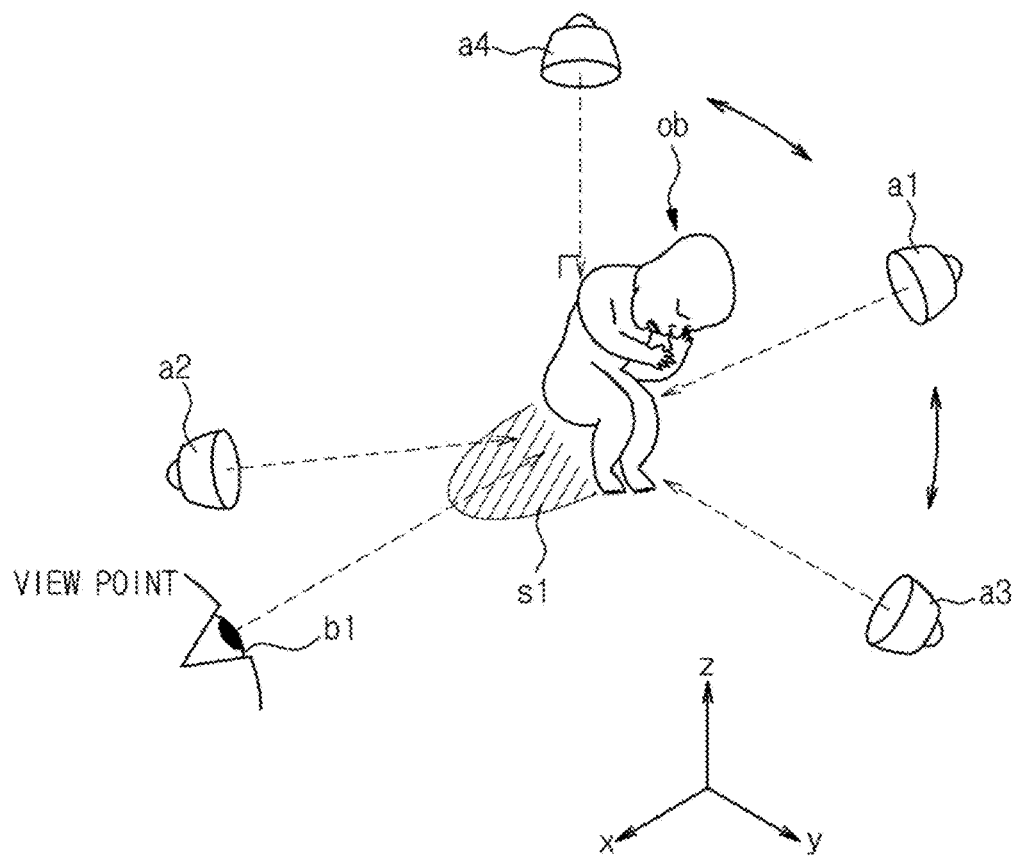
FIG. 3 is a view which illustrates an emission of virtual illumination toward an object.

According to one or more exemplary embodiments, the rendering unit 110 may perform rendering by using information which relates to a predetermined position of virtual illumination which is emitted toward the object ob, i.e., a shadow map which is generated based on the predetermined position of the virtual illumination. In this regard, the position of the virtual illumination indicates information which relates to a position at which illumination is to be virtually emitted toward the object ob as illustrated in FIG. 3. In addition, a shadow map is a result of mapping a resultant texture of the rendered shadows, which reflect a shape of the object ob, to an image of the object ob, when illumination is emitted toward the object in the image from a particular position.

According to one exemplary embodiment, the rendering unit 110 may generate the above-described shadow map based on the predetermined position of the virtual illumination and then perform rendering by using the generated shadow map.

In this case, the rendering unit 110 may perform rendering by receiving the position of the virtual illumination from the virtual illumination processor 130 of FIG. 2, generating a shadow map based on the received position of the virtual illumination, and adding the generated shadow map to volume data. In addition, the rendering unit 110 may read out the position of virtual illumination which is stored in a separate storage space connected to the rendering unit 110, e.g., a volatile memory or a non-volatile memory, generate a shadow map based thereon, and perform rendering by using the shadow map, in order to generate a shaded 3D image. In this case, the position of virtual illumination that is received or read out by the rendering unit 110 may be expressed or denoted as coordinates ($\theta$, $\varphi$) which are represented in a spherical coordinate system as described below.

In order to generate a shadow map, the rendering unit 110 may include a shadow processor 111 as illustrated in FIG. 2. The shadow processor 111 generates a shadow map which is used for rendering of image data collected from the object ob, in particular, volume data, so that the rendering unit 110 performs volume rendering by using the generated shadow map.

For example, the shadow processor 111 may determine a direction of a shadow to be added to the object ob based on the position of virtual illumination which is transmitted by a virtual illumination controller 131 of the virtual illumination processor 130, determine a shape of the shadow to be added, based on the position of virtual illumination and the shape of the object ob, and generate a shadow map to be used in rendering based on the determination results.

After the shadow processor 111 generates the shadow map, the rendering unit 110 reconstructs an image of the object ob to which a predetermined shadow is added, e.g., a 3D image, by applying the generated shadow map to the rendering of the image data. Because the shadow is represented on the generated 3D image, the image of the object ob may be more realistically displayed.

In another exemplary embodiment, the rendering unit 110 may receive a shadow map from a separate storage device or the virtual illumination processor 130 without directly generating a shadow map and then use the received shadow map in a rendering process.

In addition, the rendering unit 110 may perform rendering of volume data by using any one or more of various other methods in addition to shadow mapping so that a shadow is formed on the rendered image.

As illustrated in FIG. 2, the image processor 100 may include the projection image acquisition unit 120 which is configured to generate a projection image which corresponds to a predetermined view point based on the image data rendered by the rendering unit 110 or a result image which has been corrected by the image correction unit 140, which will be described below.

When image data which relate to the object ob are volume data which relate to the object ob which data include 3D information, the projection image acquisition unit 120 acquires a 2D image (i.e., projection image) which corresponds at least one view point, i.e., at least one angle, based on a 3D image of the object ob which is obtained via volume rendering which is performed by the rendering unit 110, or based on a 3D image which has undergone volume rendering and been corrected by the image correction unit 140. In this regard, the view point of the object ob may be predetermined based on a setting that is preset in the image processing apparatus M, or may be input by a user via any one or more of various kinds of input units (i.e., an input unit 101) which are installed in the image processing apparatus M or connected thereto via a wired or wireless communication network, such as, a keyboard, a mouse, a touch screen, a trackball, and/or the like.

The virtual illumination processor 130 of the image processor 100 transmits various data for the virtual illumination, e.g., position information which relates to the virtual illumination, to the rendering unit 110 or the image correction unit 140, so that the rendering unit 110 or the image correction unit 140 reconstructs a 3D image to which a shadow which relates to the virtual illumination is applied and/or corrects luminance and/or contrast of the acquired 3D image.

Figure 4A:
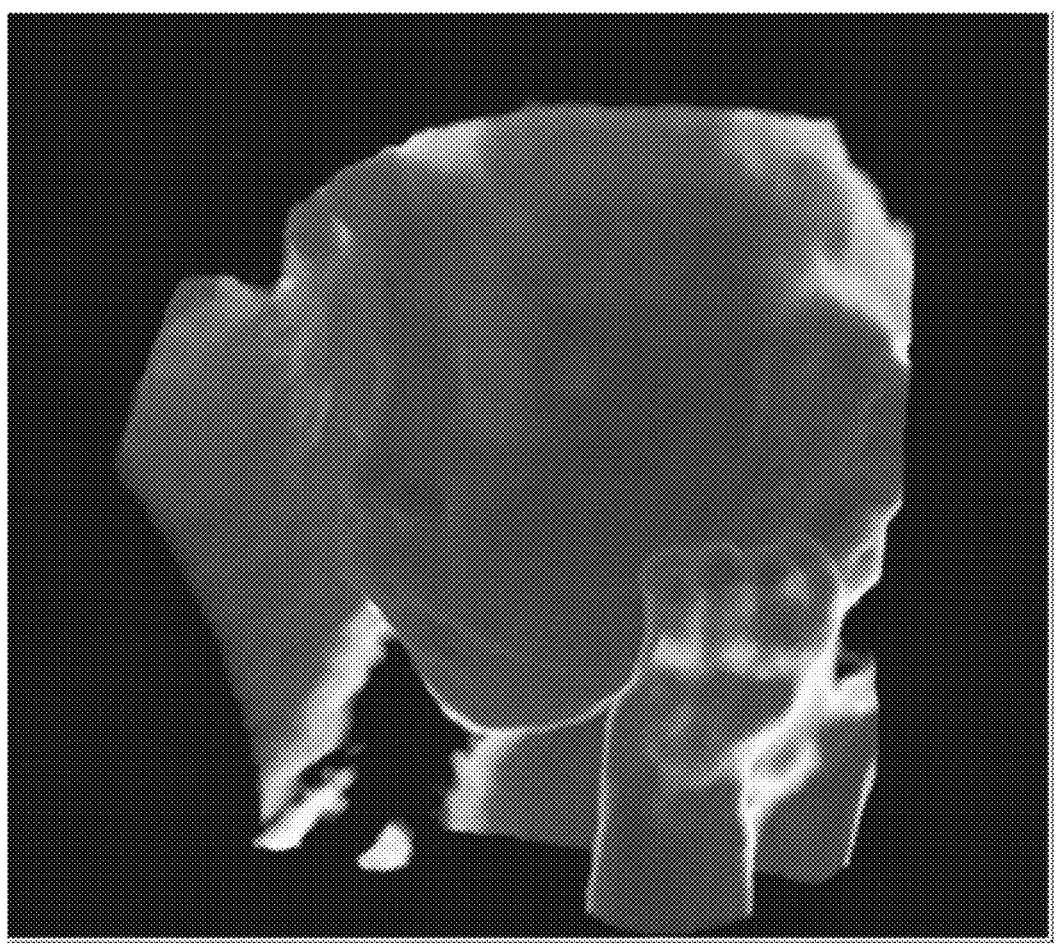
FIGS. 4A and 4B illustrate images which are respectively acquired by emitting virtual illumination toward rear and front surfaces of the object.
Figure 4B:
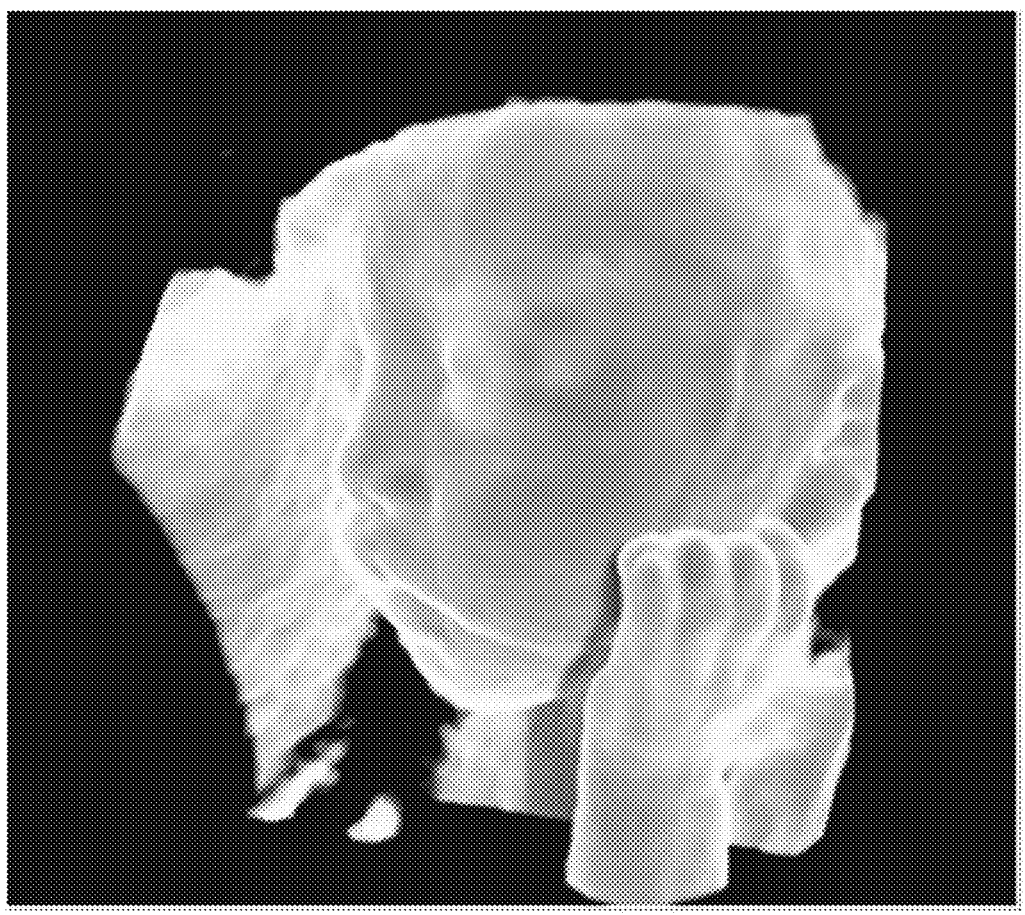

FIG. 3 is a view which illustrates an emission of virtual illumination toward an object ob. FIGS. 4A and 4B illustrate images acquired by emitting virtual illumination toward rear and front surfaces of the object ob.

As illustrated in FIG. 3, when an illumination unit irradiates the object ob with light from a predetermined position, e.g., a first position a1, a shadow s1 of the object ob is generated in a direction which is opposite to a direction of the illumination unit (i.e., an X-axis direction) with respect to the object ob. In this case, when a view point b1 is located in the direction which is opposite to direction of the illumination unit with respect to the object ob, the object ob appears dark due to the shadow s1 from the view point. By contrast, in a case in which the illumination unit irradiates the object ob with light from a second position a2, when the view point b1 is located in the same direction or approximately the same direction as that of the illumination unit or at a position which is relatively nearby to that of the illumination unit, the object ob appears brighter due to increased luminance.

A virtual illumination unit virtually emits light toward the object ob, similarly as would be emitted by an actual illumination unit. Thus, even when virtual illumination is emitted, image processing is needed in order to display a shadow, rim light, or the like similarly to a case in which actual illumination is emitted.

In particular, as illustrated in FIG. 4A, when virtual illumination is emitted from a rear direction $v_1$ (see also FIG. 5) with respect to the object ob, i.e., when the virtual illumination includes backlight, an edge of the object ob distinctly appears relatively bright due to backlight derived from the virtual illumination, and a central region of the object ob appears relatively darker.

By contrast, as illustrated in FIG. 4B, when virtual illumination is emitted from a front surface of the object ob, i.e., when virtual illumination includes front light, a central region of the object ob appears relatively bright, whereas a contrast quality of the acquired image or 3D properties thereof may be reduced due to increased luminance and light scattering.

The virtual illumination processor 130 stores and/or processes various types of information which relate to the virtual illumination, e.g., information which relates to a predetermined emission direction or distance of the virtual illumination, i.e., a position of the virtual illumination unit, the amount of the virtual illumination, and the like, and transmits the various information which relates to the virtual illumination to the rendering unit 110 and/or to the image correction unit 140. In accordance with the transmitted information which relates to the virtual illumination, the rendering unit 110 and/or the image correction unit 140 may generate a shadow or the like in a 3D image of the object ob, and/or correct the size or concentration of shadow, brightness of the object ob, or the like.

As illustrated in FIG. 2, the virtual illumination processor 130 may include the virtual illumination controller 131, a coordinate converter 132, and a storage unit 133.

The virtual illumination controller 131 transmits various information which relates to the virtual illumination and/or control commands which relate to the virtual illumination to the rendering unit 110 or each element of the virtual illumination processor 130, e.g., the coordinate converter 132 and the storage unit 133. As desired, the virtual illumination controller 131 may receive position information which relates to the virtual illumination and/or information which relates to the amount or the like of the virtual illumination from a user via the input unit 101, and then transmit the received information to each element of the virtual illumination processor 130 or generate separate control commands based on the received information and transmit the control commands to each element of the virtual illumination processor 130. In addition, the virtual illumination controller 131 may read out various predetermined setting information and/or data which relate to the virtual illumination from a separate storage space, and then transmit the read-out information to each element thereof or generate control commands based on the information.

After the position of the virtual illumination is determined by the virtual illumination controller 132, the determined position of the virtual illumination may be transmitted to the rendering unit 110. Then, the rendering unit 110 may further add a shadow to the 3D image of the object ob based on the transmitted position of the virtual illumination.

As described above, if the rendering unit 100 reads out information which relates to the virtual illumination from a separate storage space, the virtual illumination processor 130 may receive the information which relates to the virtual illumination read by the rendering unit 110. In this case, the virtual illumination controller 131 of the virtual illumination processor 130 determines a position of the virtual illumination based on the information which relates to the virtual illumination.

When the position of the virtual illumination is represented by using a rectangular coordinate system having x, y and z axes, i.e., when position values of the virtual illumination are represented as (x, y, z), the coordinate converter 132 of the virtual illumination processor 130 converts coordinates of the virtual illumination position in the rectangular coordinate system into coordinates in a spherical coordinate system.

Figure 5:
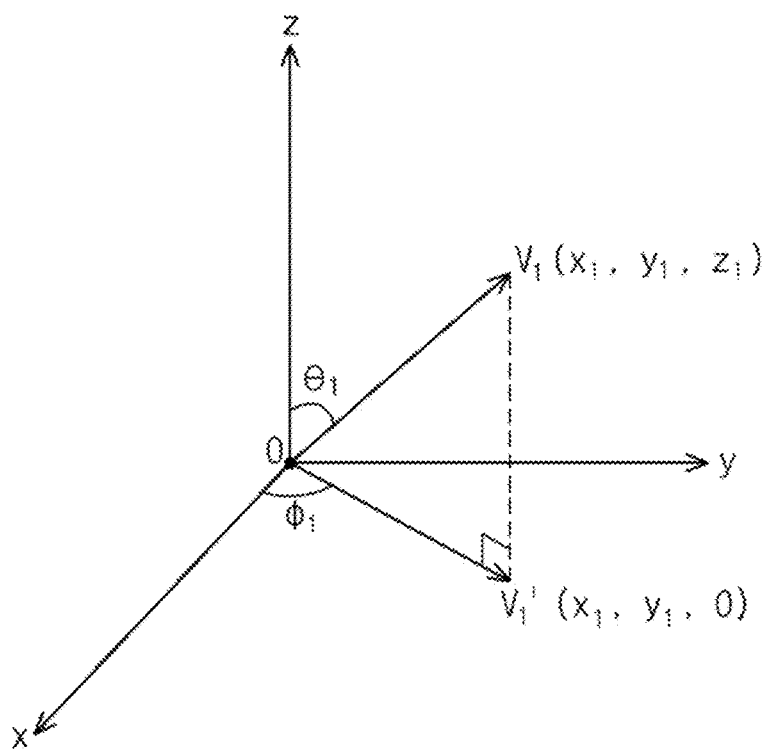
FIG. 5 is a view which illustrates a method for performing a conversion between a rectangular coordinate system and a spherical coordinate system.

FIG. 5 is a view which illustrates a method for conversion between a rectangular coordinate system and a spherical coordinate system, according to an exemplary embodiment. As illustrated in FIG. 5, it is assumed that a first virtual illumination position $v_1$ has coordinates $(x_1, y_1, z_1)$ in the rectangular coordinate system, an angle between a vector $v_1$ which corresponds to the first virtual illumination position and the z axis is $\theta_1$, and an angle between a vector $v_1'$ obtained by projecting the vector $v_1$ onto an x-y plane and the x axis is $\varphi_1$. In this case, a distance between the first virtual illumination position and the origin, i.e., an absolute value r of the vector $v_1$ for the first virtual illumination position, may be obtained by applying Equation 1 below:

$$r = \sqrt{x_1^2 + y_1^2 + z_1^2} \qquad \text{[Equation 1]}$$

In addition, the angle $\theta_1$ between the vector $v_1$ and the z axis and the angle $\varphi_1$ between the vector $v_1'$ and the x axis may be obtained by respectively applying Equations 2 and 3 below:

$$\theta_1 = \cos^{-1}\left(\frac{z_1}{r}\right) \qquad \text{[Equation 2]}$$

$$\phi_1 = \tan^{-1}\left(\frac{y_1}{x_1}\right) \qquad \text{[Equation 3]}$$

By using Equations 1, 2, and 3, the coordinates represented as $(x_1, y_1, z_1)$ in the rectangular coordinate system may be converted into $(\theta_1, \varphi_1)$, which are coordinates in the spherical coordinate system. By converting coordinates in the rectangular coordinate system into coordinates in the spherical coordinate system, the number of variables may be decreased, thereby simplifying computation.

In some exemplary embodiments, the coordinates (θ, φ) in the spherical coordinate system may not be defined as illustrated in FIG. 5. For example, the value θ may be defined as an angle between the x-y plane and the vector $v_1$. Even in this case, the coordinate (θ, φ) may be obtained using the inverse of a sine function, a cosine function, or a tangent function similarly as described above.

The virtual illumination position value (θ,φ) which is obtained by calculating and converting into the coordinates in the spherical coordinate system by using the coordinate converter 132 may be temporarily or permanently stored in the storage unit 133. The above-described rendering unit 110 or the image correction unit 140, which will be described below, may read out the converted coordinates for the virtual illumination position and then perform rendering or image correction accordingly.

The image correction unit 140 of the image processor 100 corrects an acquired image by performing predetermined image processing on the acquired image data, e.g., rendered volume data or a projection image which corresponds to at least one view point for the rendered volume data. The image correction unit 140 may receive the information which relates to the virtual illumination from the virtual illumination processor 130 as in the rendering unit 110. In this case, the information which relates to the virtual illumination may include coordinates in a spherical coordinate system, as described above. In addition, the image correction unit 140 may receive a conversion function which is appropriate for image correction by reading a conversion function database 150. The image correction unit 140 may correct volume data or a projection image which corresponds to at least one view point based on the volume data by using the received or read-out virtual illumination position and at least one conversion function (e.g., correction of luminance, contrast, hue or the like of the projection image), thereby generating a result image.

The image correction unit 140 may include a first correction unit 141, a second correction unit 142, and a third correction unit 143, as illustrated in FIG. 2.

The first correction unit 141 may be configured to adjust a brightness of image data, e.g., a projection image which is acquired by the projection image acquisition unit 120. According to one exemplary embodiment, the first correction unit 141 may read out a first conversion function F1 which is extracted from the conversion function database 150 and then adjust a brightness of the projection image by applying the first conversion function F1 to the acquired projection image. In this case, the first conversion function F1 which is applied to the projection image may include an illumination attenuation function which is used to adjust a brightness attenuation of the projection image.

In particular, in one exemplary embodiment, the first conversion function F1 may be expressible by Equation 4 below:

$$l(\varphi,\theta)=1-\beta(\varphi,\theta)$$ [Equation 4]

In this regard, β(φ,θ) (hereinafter referred to as the "β function") is a value which is determined based on the position of virtual illumination. In one exemplary embodiment, the β function used in operation of the first conversion function F1 may take the same form as a Gaussian function.

In particular, according to one exemplary embodiment, the β function may be expressible by Equation 5 below:

$$\beta(\phi, \theta) = Ae^{-\left(\frac{(\phi-\phi_0)^2}{2\sigma_\phi^2} + \frac{(\theta-\theta_0)^2}{2\sigma_\theta^2}\right)}$$ [Equation 5]

In this regard, (φ, θ) denotes coordinates which are calculated by the coordinate converter 132 or the like or a pre-given coordinate pair for the virtual illumination position in a spherical coordinate system, and (φ$_0$, θ$_0$) denotes coordinates of a reference position in the spherical coordinate system. For example, (φ$_0$, θ$_0$) may be (0, 0). In Equation 5, σ$_\varphi$ and σ$_\theta$ denote respective values which relate to a distribution of the virtual illumination position, and A denotes a constant that is predetermined based on a selection by a user, a manufacturer of the image processing apparatus M, or the like. For example, A may have a value of 1.

As represented in Equation 5, the result value of the β function, i.e., the β value, is determined as a function of the virtual illumination position, e.g., the φ and θ values. The β value, i.e., the φ and θ values, is continuously varied based on a corresponding change in the virtual illumination position.

Figure 6:
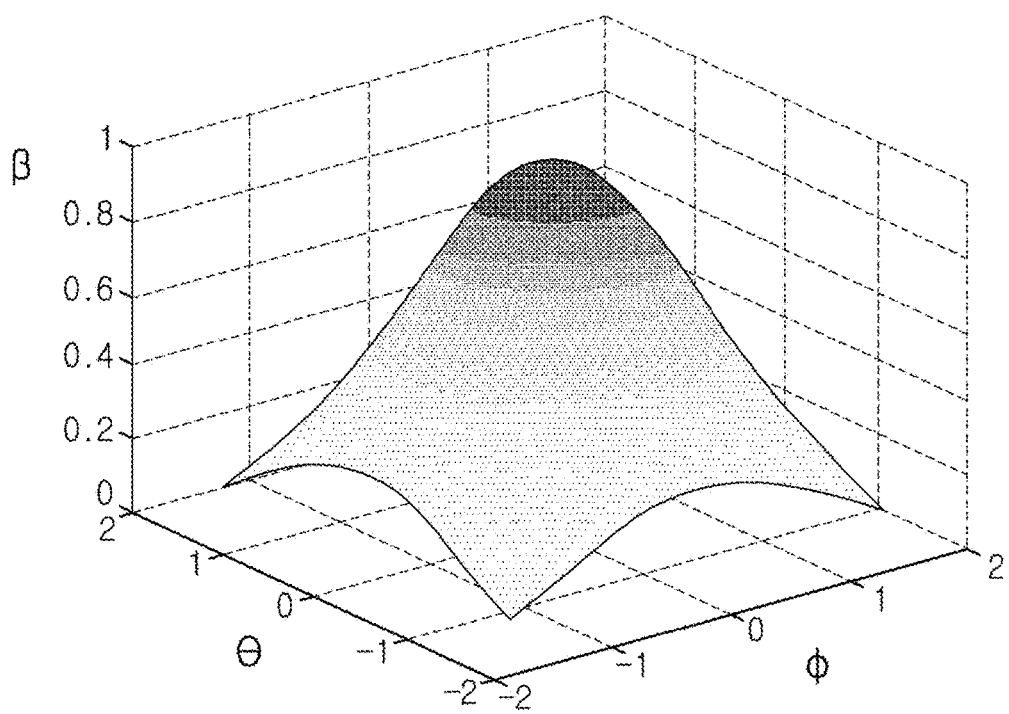
FIG. 6 is a graph which illustrates a β function, according to an exemplary embodiment.

The β function may be illustrated as a graph as shown in FIG. 6. In FIG. 6, x and y axes denote θ and φ, respectively, the z axis denotes β values, and the β values denote calculation results which are obtained by substituting the φ and θ values into the β function. As illustrated in FIG. 6, the graph for the β function has a bell shape with a protruding central portion. In this case, referring to FIG. 6, it can be confirmed that θ and φ increase when approaching zero and have the maximum values at zero. By contrast, when any one of the θ and φ values is distant from zero, i.e., when approaching 2 or –2, the β value approximates to zero.

The β function as expressed by Equation 5 is used in the first conversion function F1 as expressed by Equation 4, and second and third conversion functions F2 and F3 as expressed by Equations 8 and 9, respectively, which will be described below.

Figure 7:
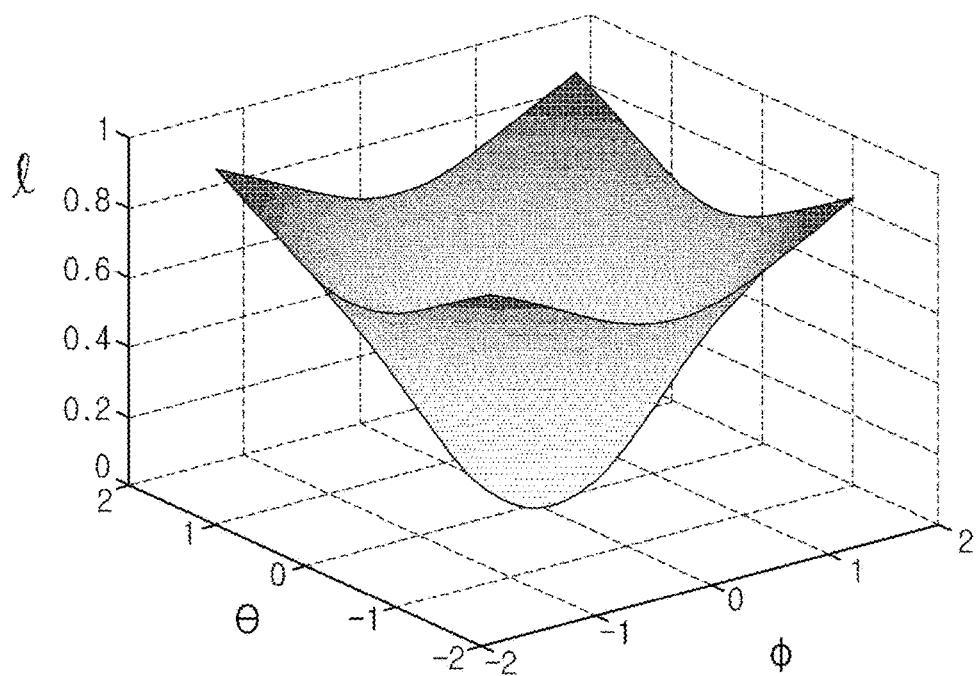
FIG. 7 is a graph which illustrates a first conversion function, according to an exemplary embodiment.

Further, the first conversion function F1 of Equation 4 may be illustrated as a graph as shown in FIG. 7. FIG. 7 is a graph of the first conversion function, i.e., the function l(φ,θ), which shows a relationship among θ and φ and a degree l of luminance attenuation. Equation 4 clearly illustrates that the result value of the first conversion function F1 may be obtained by subtracting the β function from the constant. Thus, as illustrated in FIG. 7, the first conversion function F1 may have a bell shape with a concave central portion which is different from the β function. Accordingly, the θ and φ values of the first conversion function F1 decrease when approaching zero and, consequently, the values converge to zero, by contrast with the β function illustrated in FIG. 6. When any one of the θ and φ values is distant from zero, i.e., when approaching 2 or –2, the first conversion function F1 approximates to 1. In this case, when the first conversion function F1 is applied to the projection image, the image appears dark as the θ and φ values approximate to zero. When both of the θ and φ values are equal to zero, the image is darkest. Therefore, the image may have luminance attenuation effects based on the virtual illumination position.

Figure 8:
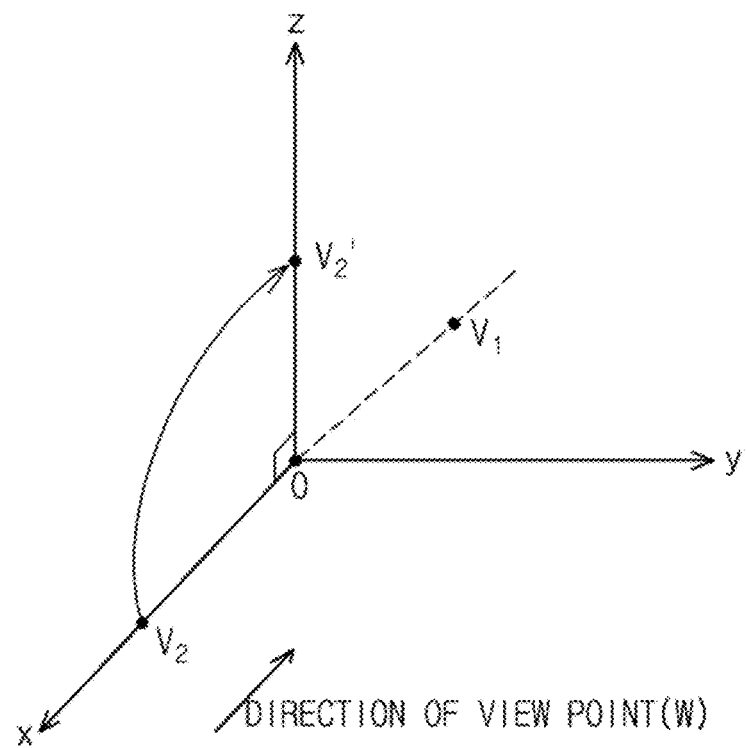
FIG. 8 is a view which illustrates a conversion of θ values.

FIG. 8 is a view which illustrates a conversion of the θ value. When both of the θ and φ values are equal to zero, as illustrated in FIG. 8, a virtual illumination position is present at a point on the z axis, e.g., $V_2'$. Thus, in a case in which the θ and φ values are defined by Equations 1, 2, and 3, θ needs to be converted prior to substitution of the θ and φ values into the first conversion function F1. In this case, when the virtual illumination is on a front side of the object, i.e., when a direction of the virtual illumination and a direction of a view point are the same or approximate to each other, first, the θ value is converted by using Equation 6 below for application to the first conversion function F1:

$$\theta' = \theta - \frac{\pi}{2} \qquad \text{[Equation 6]}$$

According to Equation 6, the θ' value is decreased by π/2 from the θ value. FIG. 7 is a view which illustrates the first conversion function F1. It is assumed that the coordinates (θ, φ) of a virtual illumination position V$_2$ in the spherical coordinate system prior to conversion are (0, π/2), as illustrated in FIG. 8. If the view point is positioned on the x axis and the object ob is located at the origin O, an emission direction of the virtual illumination at V$_2$ is the same as a direction of the view point with respect to the object ob. In particular, the virtual illumination which is emitted toward the object ob is front light. In this case, the θ value is converted by using Equation 6 in order to obtain a coordinate (0, 0). More particularly, as illustrated in FIG. 8, the virtual illumination position V$_2$ prior to conversion is transformed into a virtual illumination position V$_2$' after conversion.

The coordinate obtained by converting the θ value by using Equation 6 is applied to the first conversion function F1. Because the coordinate (θ', φ) to be applied to the first conversion function F1 is (0, 0), the result value of the first conversion function F1 approximates to zero, as seen from Equations 4, 5 and 6, whereby luminance of the projection image may be reduced as described above.

By contrast, when the virtual illumination is located on a back side, i.e., when an emission direction of the virtual illumination is relatively opposite to a direction of the view point with respect to the object ob, first, the θ value is converted by using Equation 7 below to be applied to the first conversion function F1:

$$\theta' = \theta + \frac{\pi}{2} \qquad \text{[Equation 7]}$$

According to one exemplary embodiment, the second correction unit 142 of the image correction unit 140 performs a tone mapping upon image data, e.g., the projection image acquired by the projection image acquisition unit 120. Accordingly, contrast or the like of the image data may be corrected and/or various effects may be added to the image data. Similarly as described above, the second correction unit 142 may read out the second conversion function F2, which is a tone mapping function, which is extracted from the conversion function database 150, and perform the tone mapping by applying the read-out second conversion function F2 to the image data, e.g., the projection image.

In one exemplary embodiment, the second conversion function F2 may be expressible by Equation 8 below:

$$p(x, \phi, \theta) = \frac{1}{1 + \alpha \cdot e^{-\beta(\phi,\theta)\cdot x}}. \qquad \text{[Equation 8]}$$

In Equation 8, x denotes a respective image value (i.e., an image input value) which is input to each respective pixel or voxel of an image which is collected by the image data collector 10 or acquired by the projection image acquisition unit 120. p(x,φ,θ), which is obtained as a result of the calculation, denotes a corrected image value (i.e., an image output value) that is output as a result of calculation of the image input value of each pixel or voxel by using Equation 8.

In addition, in Equation 8, φ and θ denote coordinates which are calculated by the coordinate converter 132 or the like, or pre-given coordinates for the virtual illumination position in the spherical coordinate system.

The β function of Equation 8, i.e., β(φ,θ), is a value which is determined based on the position of virtual illumination. In one exemplary embodiment, the β function may take the same form as a Gaussian function. In particular, the β function used in operation of the second conversion function F2 may be expressible by Equation 5 described above. In addition, as described above, in a case in which φ and θ are defined as illustrated in FIG. 5, first, the θ value may be converted by using Equations 6 and 7. In this case, when the virtual illumination is located at a front side of the object ob, the θ value is converted by using Equation 6, and, when the virtual illumination is located at a rear side of the object ob, the θ value is converted by using Equation 7.

As described above, Equation 8 includes the β function. Thus, as the β value which is obtained as a result of calculation by using the β function varies, the second conversion function F2 also varies. As described above, because the β value varies based on the virtual illumination position, the second conversion function F2 as expressed by Equation 8 also varies based on the virtual illumination position.

In Equation 8, α is a constant which is selectable by a user or a constant that may be preset in the image processing apparatus M or the like. The form of the second conversion function F2 of Equation 8 may also be determined by the constant α.

Figure 9:
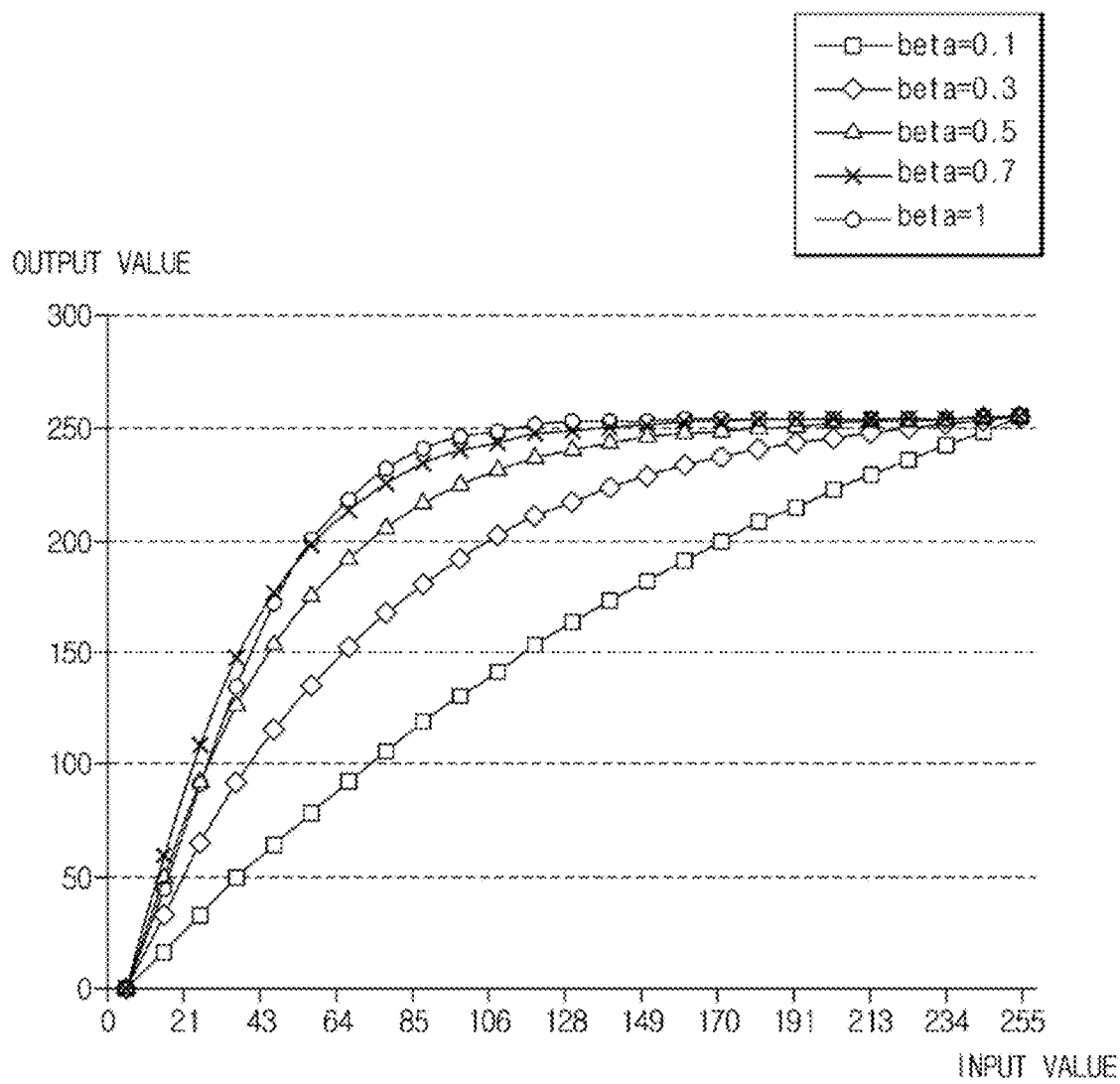
FIG. 9 is a graph which illustrates forms of a second conversion function which vary based on a change in the β value.

FIG. 9 is a graph which illustrates forms of the second conversion function F2 as expressed by Equation 8 based on a change in the β value which is obtained as a result of calculation by the β function. In FIG. 9, x axis denotes a respective image value (i.e., x in Equation 8) of each voxel or pixel of the projection image which is input to the image correction unit 140. In particular, the x-axis denotes image input values. The y-axis denotes result values which correspond to the x values obtained as a result of calculation by Equation 8. In particular, the y axis denotes a respective image output value of each voxel or pixel of the result image after correction.

As illustrated in FIG. 9, the second conversion function F2 has a concave shape. In this case, the form of the second conversion function F2 is determined based on the β value which is obtained as a result of calculation by using the β function.

As illustrated in FIG. 9, when the β value is small, e.g., beta=0.1, a plot for the second conversion function F2 is represented as a nearly linear-shaped smooth curve. In this aspect, in all of the ranges of the plot, as the image input value increases, the image output value increases approximately proportionally to the image input value. Thus, a respective image output value of each pixel or voxel that is approximately proportional or proportional to a corresponding image input value of each pixel or voxel is obtained.

As the β value increases, a curvature of the plot for the second conversion function F2 increases, as illustrated in FIG. 9. The plots have a shape which protrudes leftward and upward. In this case, when the image input values are small, e.g., in a range of between 0 and 50, the image output values are rapidly changed, even with respect to a relatively small change of the image input values. As the image input values increase to above a particular value, a respective change in the image output values based on a corresponding change in the image input values becomes slow, and, when the image input values are certain values, e.g., 120 or greater, the image output values are the same or approximate to each other in spite of the corresponding change in the image input values.

In particular, as the image input value increases, a tangent slope at each point of the second conversion function F2 gradually decreases. In this case, as illustrated in FIG. 9, as the β value of the second conversion function F2 increases, the tangent slope at each point of the second conversion function F2 rapidly decreases in correspondence with an increase of the image input value. Conversely, when the β value of the second conversion function F2 is small, the tangent slope smoothly decreases.

When the β value of the second conversion function F2 is very high, e.g., beta=1, the curvature of the plot of the second conversion function F2 is relatively large. As illustrated in FIG. 9, even when the image input value is small, a very high image output value may be obtained. In addition, when respective image input values of a plurality of pixels or voxels are small, e.g., 85 or less, a difference between corresponding image output values of the pixels or voxels is relatively large, even though a difference between the image input values of the pixels or voxels is relatively small.

As described above, the β value varies based on coordinates of the virtual illumination position, and the form of the second conversion function F2 varies based on a change in the β value, as illustrated in FIG. 9. Thus, by applying the second conversion function F2 to image data, voxel or pixel values of each image may be corrected differently from each other based on a virtual illumination position which is selected by a user or preset in the image processing apparatus M, and an image contrast may also be adjusted based on the virtual illumination position.

The third correction unit 143 of the image correction unit 140 may be configured to adjust a color (i.e., a color value) of the projection image which is acquired by the projection image acquisition unit 120. In one exemplary embodiment, the third correction unit 143 may adjust the color of the projection image by using the third conversion function F3 which is acquired by reading the conversion function database 150. In some exemplary embodiments, the third correction unit 143 may not only adjust the color value but also correct a luminance of the image. In particular, the third correction unit 143, in addition to the first correction unit 141, also corrects the luminance of the acquired image.

In particular, in one exemplary embodiment, the third conversion function F3 may be expressible by Equation 9 below:

$$C(x,s,\varphi,\theta)=x\cdot s\cdot[1-\epsilon]+\epsilon\cdot l(\varphi,\theta)]$$ [Equation 9]

In Equation 9, x denotes a respective image value of an object which is input to each voxel of image data. In particular, as described above, x is a respective image value of each voxel collected by the image data collector 10. In addition, φ and θ denote coordinates which are calculated by the coordinate converter 132 or the like or pre-given coordinates for the virtual illumination position in the spherical coordinate system.

In addition, s denotes a value of a shadow that is applied or to be applied to an image, ε denotes a separately determined luminance attenuation constant, and l(φ,θ) denotes a luminance attenuation value which is determined based on the virtual illumination position. In some exemplary embodiments, l(φ,θ) as used by the third correction unit 143 may be the same as that used by the first correction unit 141. In particular, the l(φ,θ) of Equation 9 may be determined by applying the same numerical expression as that of Equation 4.

Referring to Equation 9, the corrected image value of each voxel of the projection image according to Equation 9 may be determined by an image value of each voxel subjected to rendering by the rendering unit 110, a separately added shadow value for each voxel, and a luminance attenuation value based on the virtual illumination position. In this case, the luminance attenuation value based on the virtual illumination position may be selectable by a user, or a weight may be applied thereto by a luminance attenuation constant that is preset and pre-stored in the image processing apparatus M.

The hue of an image may be varied based on Equation 9 described above. In addition, a luminance value of the image may also be similarly changed.

As described above, the image correction unit 140 may perform image correction with respect to the acquired projection image by using the first, second, and third correction units 141, 142, and 143 sequentially according to a predetermined order, e.g., in the order of the first, second and third correction units 141, 142 and 143, or in a random order. In addition, the first, second and third correction units 141, 142 and 143 may all serve to correct the projection image, or any one or two of the first, second and third correction units 141, 142 and 143 may be configured to correct the projection image. The image correction order of the first, second, and third correction units 141, 142, and 143 or selection of at least one of the first, second and third correction units 141, 142 and 143 may be determined by a user or based on settings that are pre-stored in the image processing apparatus M.

The result images which have been corrected by the image correction unit 140 are output to the outside via the output unit 102 which is installed in the image processing apparatus M, or via any one or more of various image display devices which are provided with a display module which is connected to the image processing apparatus M via a wired or wireless communication network, e.g., a computer monitor, a notebook, a tablet PC, a smart phone, and the like. Accordingly, a user can view the corrected image of the object ob.

Figure 10A:
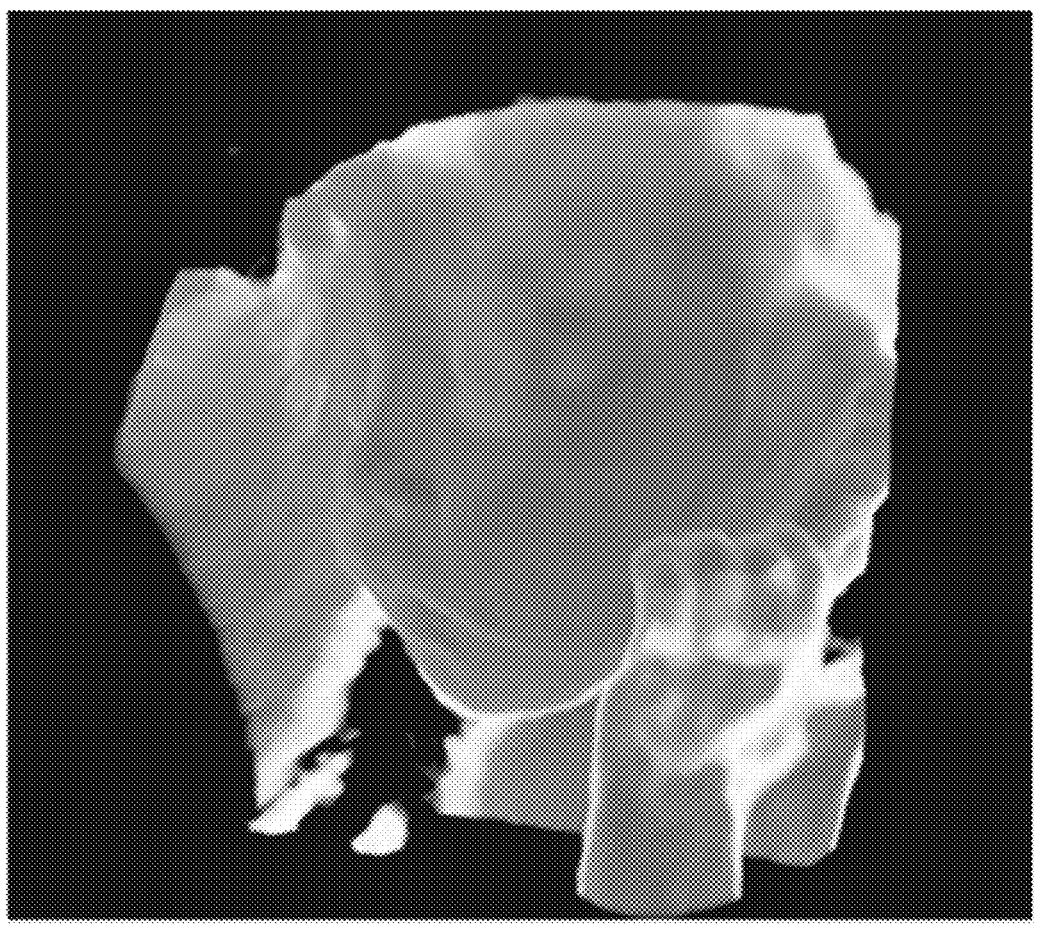
FIGS. 10A and 10B illustrate corrected images, according to an exemplary embodiment.
Figure 10B:

FIGS. 10A and 10B illustrate images which are acquired by correcting images of the object ob which are obtained when the virtual illumination is emitted respectively toward the rear and front surfaces of the object ob.

In particular, FIG. 10A illustrates an image which has been corrected by the second correction unit 142 of the image correction unit 140 in a case in which a direction of the view point is on the front side of the object ob and the virtual illumination is emitted toward the rear surface of the object ob. In this regard, the corrected image is acquired such that the second correction unit 142 performs a tone mapping with respect to the acquired projection image by using the second conversion function F2 which is expressible by Equation 9. The image shown in FIG. 10A has a relatively higher contrast than the image of FIG. 4A, and thus, the object ob, e.g., each part of the face of the fetus (e.g., eyes, nose, mouth and the like) may be more clearly recognized.

FIG. 10B is an image which has been corrected by the first and second correction units 141 and 142 of the image correction unit 140 in a case in which both of the view point and the virtual illumination unit are positioned on the front side of the object ob. In this regard, the corrected image is acquired by applying the first conversion function F1 which is expressible by Equation 4 and the second conversion function F2 which is expressible by Equation 8 to the acquired projection image. The image of FIG. 10B has a more attenuated luminance and a relatively higher contrast than those of the image of FIG. 4B, as a result of application of the first and second conversion functions F1 and F2. Thus, it can be seen that it is relatively easy to recognize the object ob, e.g., each part of the face of the fetus and the corrected image has improved 3D properties.

Figure 11:
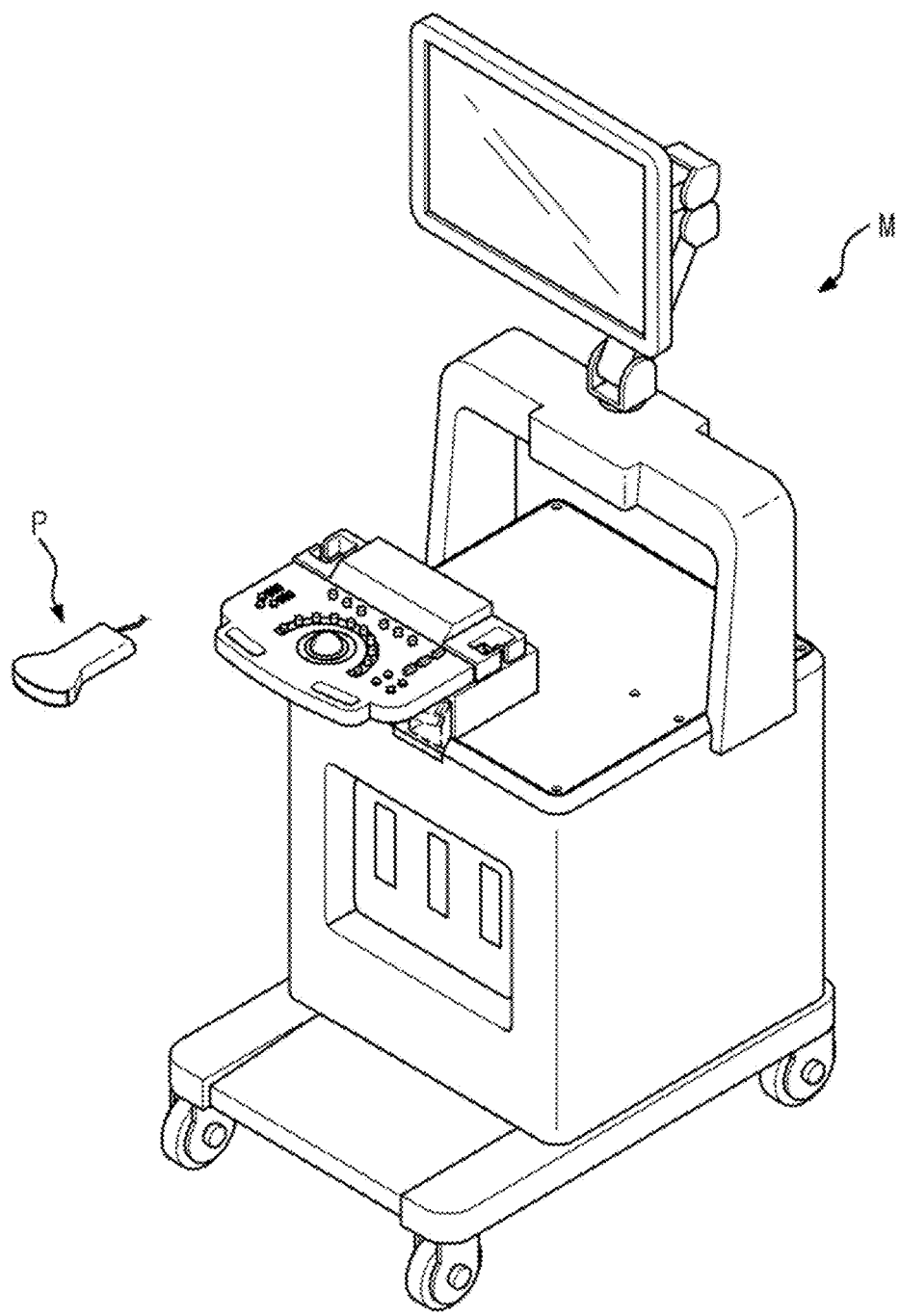
FIG. 11 is a perspective view of an ultrasonic imaging apparatus, according to an exemplary embodiment.
Figure 12:
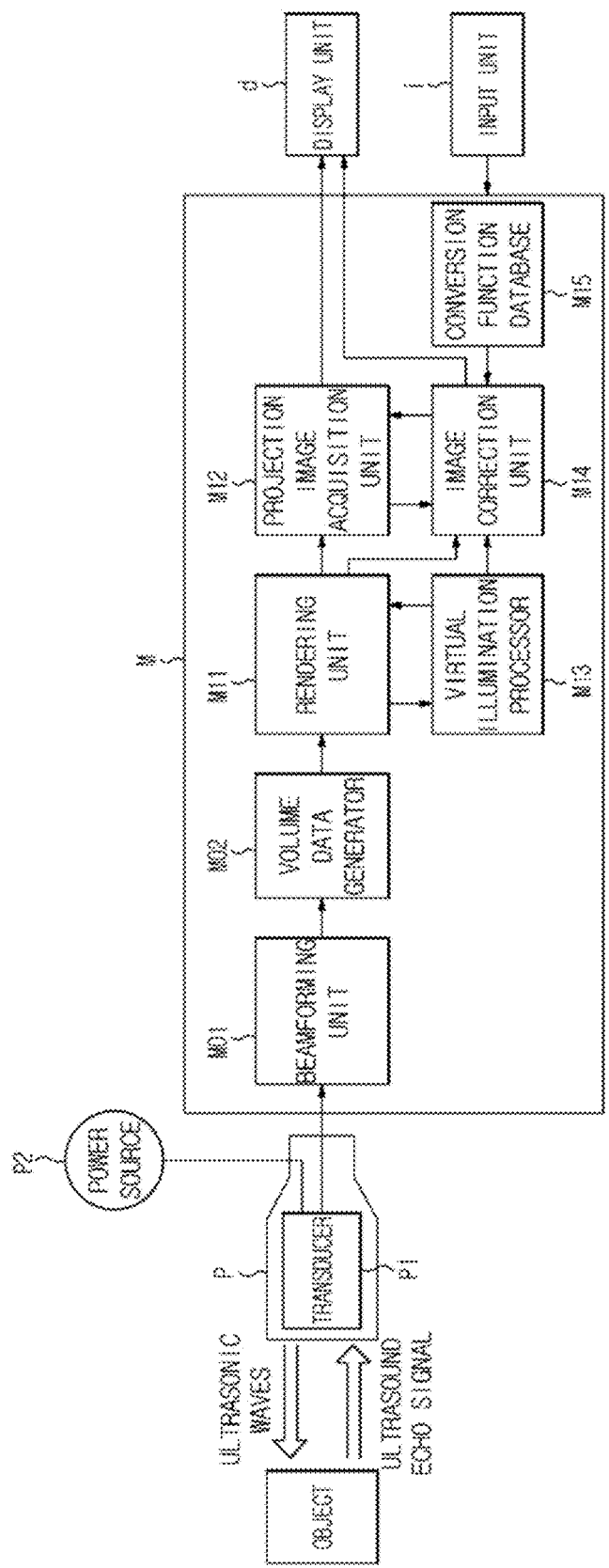
FIG. 12 is a block diagram which illustrates a configuration of the ultrasonic imaging apparatus, according to an exemplary embodiment.

FIG. 11 is a perspective view of an ultrasonic imaging apparatus, according to an exemplary embodiment. FIG. 12 is a block diagram which illustrates a configuration of the ultrasonic imaging apparatus, according to an exemplary embodiment.

The ultrasonic imaging apparatus is an imaging apparatus that transmits ultrasonic waves to an object ob, e.g., a target site inside the object ob through the surface of a human body, collects ultrasonic waves which are reflected from the target site, and generates a sectional image of various tissues or structures inside the object ob by using the collected ultrasonic waves. In particular, as illustrated in FIGS. 11 and 12, the ultrasonic imaging apparatus may include an ultrasonic probe P and a main body M.

As illustrated in FIG. 12, the ultrasonic probe P is provided at an end portion of the main body M with a plurality of ultrasound transducers P1 which are configured to generate ultrasonic waves by using alternating current which is supplied from a power source P2, direct the generated ultrasonic waves toward the object ob, receive an ultrasound echo signal which is reflected from a target site inside the object ob, and convert the received ultrasound echo signal into an electrical signal. In this regard, the power source P2 may include at least one of an external power source, a storage battery installed in the ultrasonic imaging apparatus, and/or the like. Examples of the ultrasound transducers P1 include a magnetostrictive ultrasonic transducer which uses a magnetostrictive effect of a magnetic body, a piezoelectric ultrasonic transducer which uses a piezoelectric effect of a piezoelectric material, and a capacitive micromachined ultrasonic transducer (cMUT), which transmits and receives ultrasonic waves by using vibrations of several hundreds or several thousands of micromachined thin films.

When alternating current is supplied to the ultrasound transducers P1 from the power source P2, piezoelectric vibrators or thin films of the ultrasound transducers P1 vibrate and, as a result, ultrasonic waves are generated. The generated ultrasonic waves are directed toward the object ob, e.g., into the human body. The directed ultrasonic waves are reflected by at least one target site which is located at any one or more of various depths from within the object ob. The ultrasound transducers P1 receive ultrasound echo signals which are reflected from the target site and convert the received ultrasound echo signals into an electrical signal, thereby obtaining a plurality of received signals.

The received signals are transmitted to the main body M via a wired or wireless communication network. The ultrasonic probe P receives the ultrasound echo signal via at least one of a plurality of channels, and thus the received signals are also transmitted to the main body M via at least one of the channels.

The main body M may include a beamforming unit M01 (also referred to herein as a beamformer M01), a volume data generator M02, a rendering unit M11 (also referred to herein as a renderer M11), a projection image acquisition unit M12 (also referred to herein as a projection image acquirer M12), a virtual illumination processor M13, an image correction unit M14 (also referred to herein as an image corrector M14), and a conversion function database M15. In some exemplary embodiments, however, some of the above-described elements may be omitted from the main body M.

The beamforming unit M01 performs beamforming based on the plurality of received signals. In this regard, beamforming is a process of focusing a plurality of received signals which are input via at least one of a plurality of channels in order to acquire an appropriate ultrasound image of the interior of the object ob.

The beamforming unit M01 corrects a time difference in the received signals which is caused by a difference in distances between each ultrasound transducer P1 and the target site inside the object ob. In addition, the beamforming unit M01 emphasizes a plurality of received signals of a specific channel and/or relatively attenuates a plurality of received signals of another channel, thereby focusing the received signals. In this case, the beamforming unit M01 may emphasize and attenuate specific received signals by or without, for example, adding a predetermined weight to the received signals which are input via each channel.

In addition, the beamforming unit M01 may focus a plurality of received signals which are collected by the ultrasonic probe P for each of a plurality of frames by considering a position and a focal point of a conversion element of the ultrasonic probe P.

Further, beamforming which is performed by the beamforming unit M01 may include data-independent beamforming and/or adaptive beamforming.

The volume data generator M02 generates ultrasound image data based on the signals focused by the beamforming unit M01. When the beamforming unit M01 focuses a plurality of received signals for each frame, a plurality of ultrasound image data which respectively correspond to each frame is generated based on the focused signals. In this regard, the generated ultrasound image data may include 3D ultrasound image data which relate to the object ob, i.e., volume data which relate to the object ob.

The rendering unit M11 renders ultrasound image data, e.g., volume data which relate to the object ob, in order to reconstruct a 2D or 3D image of the object ob. When the image data collected by the image data collector 10 are volume data, the rendering unit M11 performs volume rendering by using the volume data. In addition, the rendering unit M11 may reconstruct an image by applying, to the rendering process, a shadow map which is generated based on the position of virtual illumination that is received by the virtual illumination processor M13 or is stored beforehand. In this regard, the rendering unit M11 may receive a shadow map from the outside or generate a shadow map based on the position of virtual illumination received by the virtual illumination processor M13. The rendering unit M11 may reconstruct a shaded 3D image through such shadow mapping.

In one exemplary embodiment, the ultrasonic imaging apparatus may further include the projection image acquisition unit M12. The projection image acquisition unit M12 may acquire a 2D image of the object ob which corresponds to at least one view point based on the 3D image subjected to volume rendering by the rendering unit M11. In this regard, the at least one view point may be input via an external input unit i and may also be determined based on settings stored in the ultrasonic imaging apparatus.

In another exemplary embodiment, the projection image acquisition unit M12 may acquire a projection image for the result image which is corrected by the image correction unit M14, which will be described below.

The virtual illumination processor M13 transmits information which relates to a position of virtual illumination to be emitted toward the object ob, i.e., a virtual illumination position, to the rendering unit M11, the image correction unit M14, or the like. The rendering unit M11, having received the virtual illumination position, performs volume rendering by applying a shade based on the virtual illumination, and the image correction unit M14 corrects an image of the object ob, e.g., a projection image, by using the virtual illumination.

According to one or more exemplary embodiments, the virtual illumination processor M13 may determine the position of the virtual illumination which is emitted toward the object ob based on instructions or commands which are received via the input unit i from a user. In another exemplary embodiment, information which relates to the virtual illumination during shadow mapping performed by the rendering unit M11 is received from the rendering unit M11, and the position of the virtual illumination to be used in the image correction unit M14 may be determined based on the received information which relates to the virtual illumination.

In addition, when the determined virtual illumination position is represented in a rectangular coordinate system, the virtual illumination processor M13 may transform the coordinates in the rectangular coordinate system into coordinates in a spherical coordinate system. In this case, coordinate conversion of the virtual illumination may be performed by using Equations 1, 2, and 3 as described above.

The image correction unit M14 corrects the volume data which is subjected to rendering performed by the rendering unit M11 or the projection image acquired by the projection image acquisition unit M12. In this case, the image correction unit M14 receives the virtual illumination position from the virtual illumination processor M13 and corrects the image by using the received virtual illumination position.

The image correction unit M14 first receives conversion functions for use in performing image correction by reading the conversion function database M15 connected thereto. In this case, the conversion functions may include at least one of the first, second and third conversion functions F1, F2 and F3.

In order to correct a luminance of the acquired image, for example, the image correction unit M14 calls the first conversion function F1 which is expressible by Equation 4 from the conversion function database M15 and substitutes the virtual illumination position received from the virtual illumination processor M13 into the first conversion function F1, thereby correcting the luminance of the acquired image.

In order to correct a contrast of the acquired image, for example, the image correction unit M14 calls the second conversion function F2 which is expressible by Equation 8 and substitutes the virtual illumination position into the second conversion function F2, thereby correcting the contrast of the image.

In order to correct a hue of the acquired image, for example, the image correction unit M14 calls the third conversion function F3 which is expressible by Equation 9 and substitutes the virtual illumination position into the third conversion function F3, thereby correcting the hue of the image.

In this regard, the image correction unit M14 may correct the luminance, the contrast, and the hue of the image at once, or the image correction unit M14 may correct only any one or two of the luminance, the contrast, and the hue of the image.

In addition, in order to correct the luminance, the contrast, and/or the hue of the image, the image correction unit M14 may first calculate the $\beta$ value that is used in Equations 4, 8 and 9. In this regard, the $\beta$ value may be determined by applying a $\beta$ function which is expressible by Equation 5.

The image correction unit M14 corrects the volume data of the object ob or the projection image of the object ob which corresponds to at least one view point by using the received or read-out virtual illumination position and the first, second and third conversion functions F1, F2 and F3, thereby generating a result image. In this regard, the result image may include a 2D image. In some exemplary embodiments, predetermined image processing may be further performed on the result image in order to generate a stereoscopic image.

The generated result image is displayed on a display unit d which is installed in the ultrasonic imaging apparatus or connected thereto via a wired or wireless communication network, e.g., a display module such as a monitor, a tablet PC, a smart phone, or the like. An example of the result image which may be displayed on the display unit d is illustrated in each of FIG. 10A and FIG. 10B.

Although FIGS. 11 and 12 illustrate that the main body M includes the beamforming unit M01, the volume data generator M02, the rendering unit M11, the projection image acquisition unit M12, the virtual illumination processor M13, the image correction unit M14, and the conversion function database M15, exemplary embodiments are not limited thereto. In particular, the main body M need not include all of the above-listed elements. Some of the elements may also be installed in another part of the ultrasonic imaging apparatus, e.g., the ultrasonic probe P.

For example, the ultrasonic imaging apparatus may include the beamforming unit M01, the volume data generator M02, the rendering unit M11, the projection image acquisition unit M12, the virtual illumination processor M13, the image correction unit M14, and the conversion function database M15, so that the ultrasonic probe P is configured to generate an ultrasound image based on an electrical signal by a predetermined process and to correct the generated ultrasound image. In addition, an information processor which is connected to the main body M or the like may include some of the above-listed elements, e.g., the conversion function database M15, and the main body M may include the beamforming unit M01, the volume data generator M02, the rendering unit M11, the projection image acquisition unit M12, the virtual illumination processor M13, and the image correction unit M14.

Figure 13:
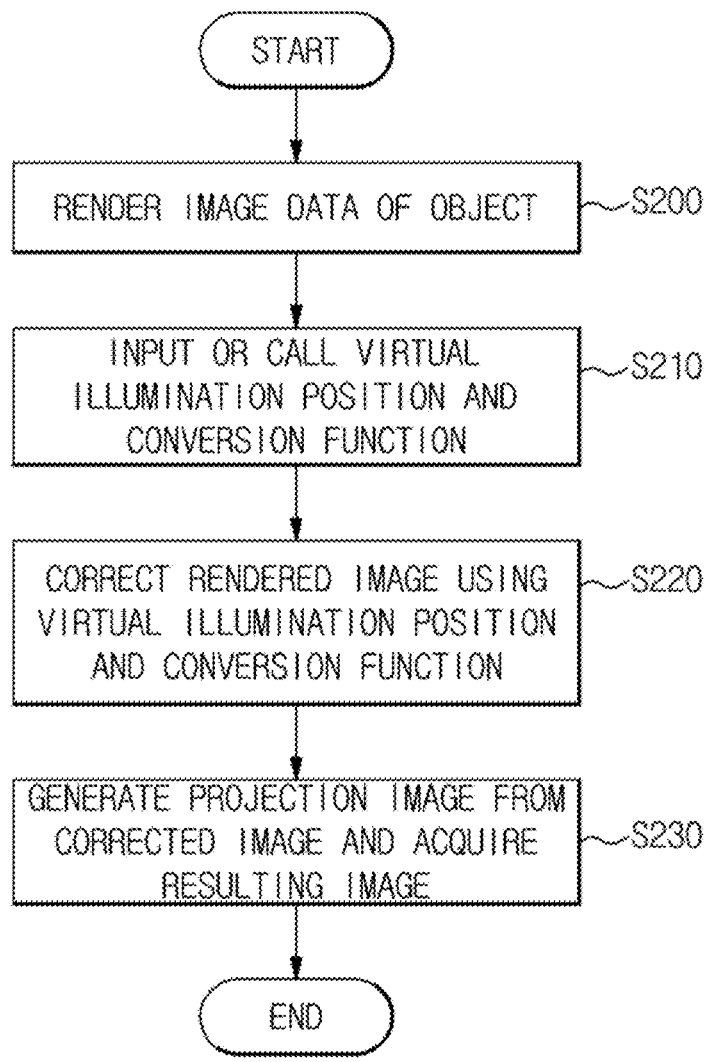
FIG. 13 is a flowchart which illustrates an image processing method, according to an exemplary embodiment.

FIG. 13 is a flowchart which illustrates an image processing method, according to an exemplary embodiment.

As illustrated in FIG. 13, in the image processing method according to an exemplary embodiment using virtual illumination, first, in operation S200, the image processing apparatus performs rendering of collected image data which relates to an object ob in order to reconstruct a 2D or 3D image of the object ob. In this case, when the collected image data are volume data, volume rendering is performed. In some exemplary embodiments, volume rendering may be performed by applying a shadow map for a shadow at a predetermined virtual illumination position with respect to the image data, i.e., shadow mapping.

In this regard, the virtual illumination position of the object ob is determined by external input or based on settings that are preset in the image processing apparatus. When shadow mapping is performed, in operation S210, the virtual illumination position of the object ob may be determined based on the position of virtual illumination used during shadow mapping. When the virtual illumination position is represented by coordinates in a rectangular coordinate system, the coordinates in the rectangular coordinate system may be converted into coordinates in a spherical coordinate system, thereby obtaining a virtual illumination position which is represented by coordinates in the spherical coordinate system.

In addition, at least one conversion function is simultaneously input or called. In this regard, the input or called conversion function may be expressible by at least one of Equation 4, Equation 8, and Equation 9. In this regard, each of Equation 4, Equation 8, and Equation 9 includes the β value which is expressible by Equation 5, and the β value varies based on the virtual illumination position, and thus, the at least one conversion function varies based on the virtual illumination position.

In operation S220, the determined virtual illumination position is substituted into the input or called conversion function and then the rendered image is corrected by using the at least one conversion function.

As a result, the resulting corrected image is acquired in operation S230. In this regard, when the corrected image includes a 3D image, the acquired image may include a 2D projection image which is generated for the corrected image. In addition, in at least one exemplary embodiment, predetermined image processing may be further performed on the corrected rendered image in order to generate a stereoscopic image as the result image.

Figure 14:
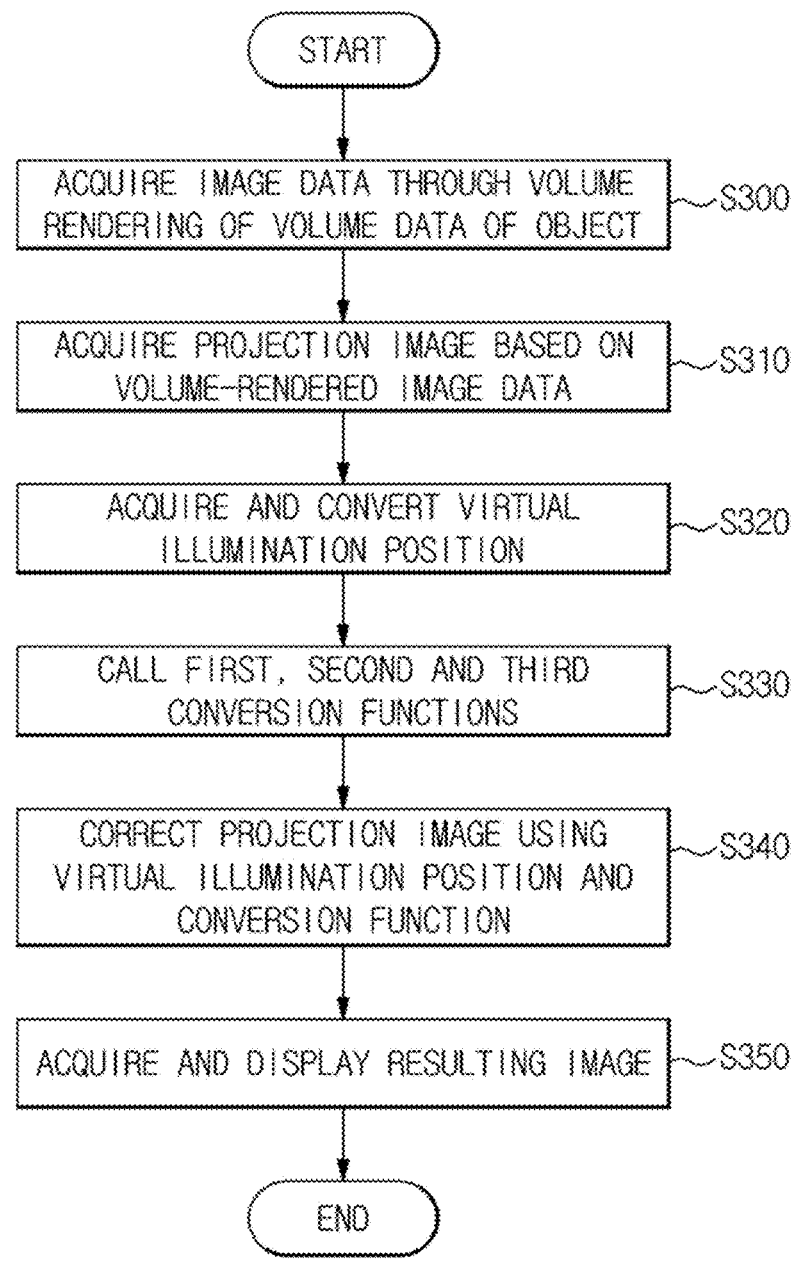
FIG. 14 is a flowchart which illustrates an image processing method, according to another exemplary embodiment.

FIG. 14 is a flowchart which illustrates an image processing method, according to another exemplary embodiment.

As illustrated in FIG. 14, in operation S300, volume rendering is performed upon the collected volume data which relates to an object ob in order to obtain 3D image data. Subsequently, in operation S310, a projection image which corresponds to at least one view point may be acquired by calculation which is based on the 3D image data which has been subjected to the volume rendering process. Even in the present exemplary embodiment, the volume rendering process may be performed in conjunction with the shadow mapping process, similarly as has been described above.

Next, in operation S320, a virtual illumination position of the object ob is determined. In this case, the virtual illumination position may be input from the outside. When shadow mapping is performed upon the volume data, in operation S320, the virtual illumination position of the object ob may be determined based on the position of virtual illumination used during the shadow mapping process. When the virtual illumination position is represented by coordinates in a rectangular coordinate system, the coordinates in the rectangular coordinate system may be converted into coordinates in a spherical coordinate system.

In operation S330, at least one of the first, second and third conversion functions F1, F2 and F3 is called as desired. In this regard, the first conversion function F1 may be called in order to correct a luminance of the acquired image, and the second conversion function F2 may be called in order to correct a contrast of the acquired image. In addition, the third conversion function F3 may be called in order to correct a hue of the acquired image. In this regard, the first conversion function F1 may be expressible by Equation 4, the second conversion function F2 may be expressible by Equation 8, and the third conversion function F3 may be expressible by Equation 9.

In operation S340, the determined virtual illumination position is substituted into the at least one of the first, second and third conversion functions F1, F2 and F3 and the received projection image is corrected by using the conversion functions based on the virtual illumination position.

As a result, in operation S350, the result image is acquired and the acquired image is displayed to a user via a display device.

Figure 15:
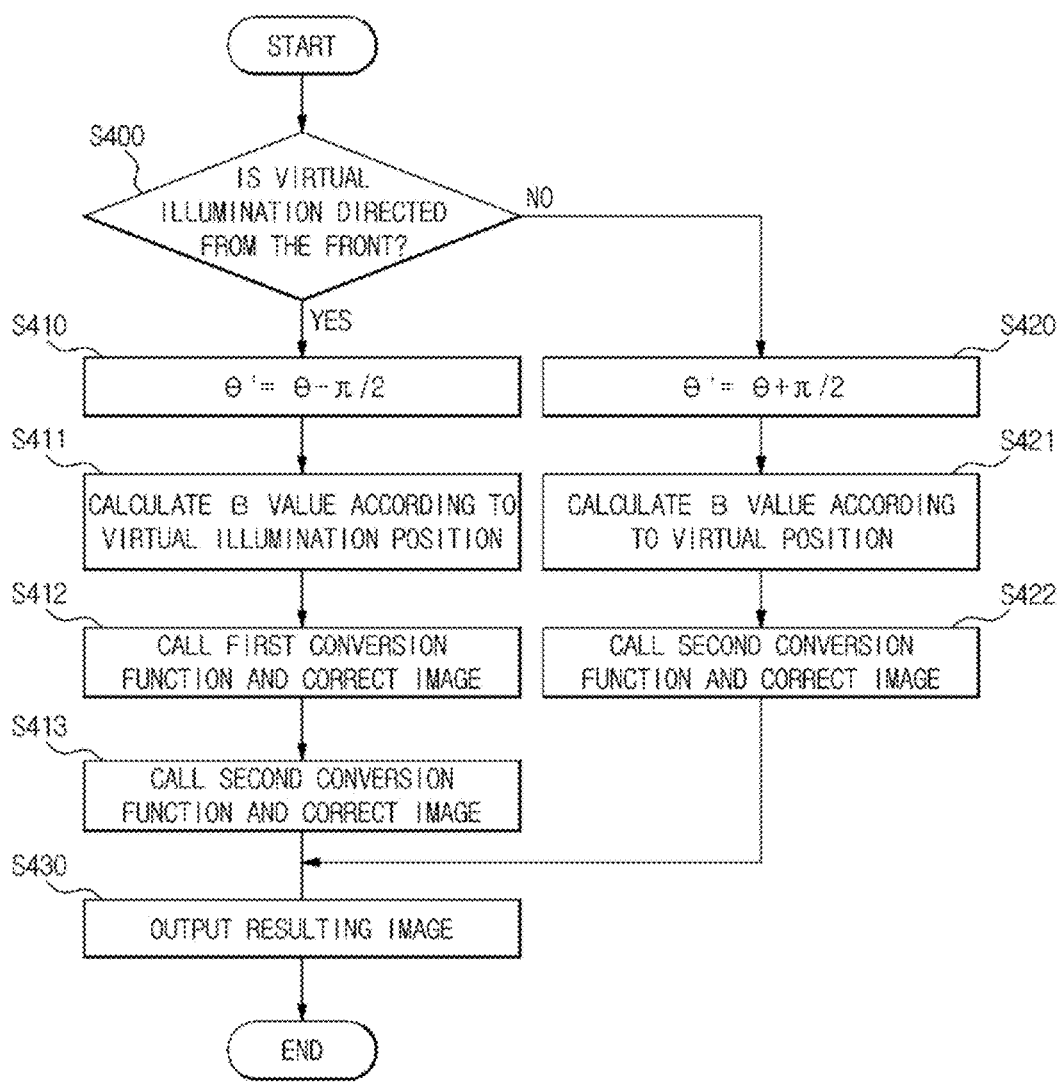
FIG. 15 is a flowchart which illustrates a process for correcting an image based on a virtual illumination position.

FIG. 15 is a flowchart which illustrates a process for correcting an image based on a virtual illumination position.

In one exemplary embodiment, when a determination is made in operation S400 that the virtual illumination position that is input by a user or determined based on settings that are preset in the image processing apparatus is the same or approximately the same as a direction of the view point, i.e., when the virtual illumination unit is positioned at a position a3 (see FIG. 3) such that the virtual illumination is directed toward the front of the object, first, in operation S410, the θ value may be converted according to Equation 6 in order to obtain a θ' value for the application of the first, second and third conversion functions F1, F2 and F3.

Then, in operation S411, the β value is calculated based on the generated virtual illumination position (θ', φ). In one exemplary embodiment, the β value may be expressible by Equation 5 as described above.

For example, in operation S412, the first conversion function F1 which is expressible by Equation 4 is called, and the image is corrected by using the first conversion function F1. In this regard, the first conversion function F1 includes the β value as described above and the β value varies based on the virtual illumination position, and thus, the first conversion function F1 also varies based on the virtual illumination position. As a result of this correction, the luminance of the image is corrected.

Subsequently, for example, in operation S413, the second conversion function F2 which is expressible by Equation 8 is called, and then the image is corrected by using the second conversion function F2. Similarly, the second conversion function F2 also includes the β value and thus varies based on the virtual illumination position. As a result of this correction, the contrast of the image is corrected.

In another exemplary embodiment, when a determination is made in operation S400 that the virtual illumination position that is input by a user or determined based on settings that are preset in the image processing apparatus is approximately opposite to a direction of the view point with respect to the object ob, i.e., when the virtual illumination unit is positioned at a position a1 (see FIG. 3) such that the virtual illumination is directed from a back side with respect to the object, first, in operation S420, the θ value may be converted according to Equation 7 in order to obtain a θ' value for application of the first, second and third conversion functions F1, F2 and F3.

Subsequently, in operation S421, the β value is calculated based on the generated virtual illumination position. The β value may be expressible by Equation 5 as described above.

When the virtual illumination is positioned in a direction which is approximately opposite to that of the view point with respect to the object, only the second conversion function F2 may be called, as illustrated in FIG. 15, in order to enhance image contrast. Then, in operation S422, the image processing apparatus corrects the image by using the called second conversion function F2.

In operation S430, the corrected result image is externally displayed on a display device or the like. Thus, a user can view the image with a luminance, contrast, and/or hue value that is corrected based on the virtual illumination position.

As is apparent from the above description, according to the image processing apparatus and method, an image of an object may be naturally displayed based on a change in the position of virtual illumination, and an image with improved quality may be acquired.

In addition, in image processing of an image which is subjected to volume rendering, 3D properties, luminance, hue, and/or contrast of an image may be improved by applying at least one conversion function that varies based on the position of virtual illumination, whereby the image may be more realistically displayed.

Moreover, when the virtual illumination unit is located at a rear side of the object, an image of the object which has a semi-transparent effect may be generated. When the virtual illumination is emitted toward the object from a front side of the object, an image which has high contrast may be generated. Therefore, an image which has excellent readability may be provided to a user.

Although a few exemplary embodiments have been shown and described, it will be appreciated by those skilled in the art that changes may be made in these exemplary embodiments without departing from the principles and spirit of the present inventive concept, the scope of which is defined in the claims and their equivalents.

What is claimed is:

1. An image processing method comprising:
performing, by an image processing apparatus, volume rendering of volume data which relate to an object and acquiring volume-rendered image data;
acquiring information which relates to a virtual illumination position;
determining at least one conversion function from a plurality of conversion functions stored in a database, based on the virtual illumination position which relates to the object; and
correcting the acquired image data by using the virtual illumination position and the at least one conversion function,
wherein the correcting comprises performing a tone mapping with respect to the acquired image data by using a second conversion function using a difference between coordinates of the virtual illumination position and coordinates of a reference position, and a distribution of the virtual illumination position.

2. The image processing method according to claim 1, wherein the correcting further comprises adjusting a brightness of the acquired image data by using a first conversion function which is determined based on the coordinates of the virtual illumination position.

3. The image processing method according to claim 2, wherein the first conversion function includes an illumination attenuation function.

4. The image processing method according to claim 2, wherein the first conversion function includes a function which is expressible by Equation 1 below:

$$l(\phi, \theta) = 1 - Ae^{-\left(\frac{(\phi-\phi_0)^2}{2\sigma_\phi^2} + \frac{(\theta-\theta_0)^2}{2\sigma_\theta^2}\right)}$$ [Equation 1]

wherein $(\varphi,\theta)$ denotes respective coordinates of the virtual illumination position in a spherical coordinate system, $(\varphi_0,\theta_0)$ denotes respective coordinates of a reference position in the spherical coordinate system, $\sigma_\varphi$ and $\sigma_\theta$ denote respective values which relate to a distribution of a first virtual illumination position, and A denotes a predetermined constant.

5. The image processing method according to claim 1, wherein the second conversion function includes a function which is expressible by Equation 2 below:

$$p(x, \phi, \theta) = \frac{1}{1 + \alpha \cdot e^{-\beta(\phi,\theta)x}}$$ [Equation 2]

wherein x denotes an image value of a respective voxel, $\varphi$ and $\theta$ denote respective coordinates of the virtual illumination position in a spherical coordinate system, a denotes a predetermined constant, and $\beta(\varphi,\theta)$ denotes a value which is determined based on the virtual illumination position.

6. The image processing method according to claim 5, wherein the $\beta(\varphi,\theta)$ is determined by applying Equation 3 below:

$$\beta(\phi, \theta) = Ae^{-\left(\frac{(\phi-\phi_0)^2}{2\sigma_\phi^2} + \frac{(\theta-\theta_0)^2}{2\sigma_\theta^2}\right)}$$ [Equation 3]

wherein $(\varphi_0,\theta_0)$ denotes respective coordinates of a reference position in the spherical coordinate system, $\sigma_\varphi$ and $\sigma_\theta$ denote respective values which relate to a distribution of a first virtual illumination position, and A denotes a predetermined constant.

7. The image processing method according to claim 1, wherein the correcting further comprises performing a hue correction with respect to the acquired image data by using a third conversion function which is determined based on the coordinates of the virtual illumination position.

8. The image processing method according to claim 7, wherein the third conversion function includes a function which is expressible by Equation 4 below:

$$C(x,s,\varphi,\theta) = x \cdot s \cdot [(1-\epsilon) + \epsilon \cdot l(\varphi,\theta)]$$ [Equation 4]

wherein x denotes an image value of a respective voxel, s denotes a shadow value, $\varphi$ and $\theta$ denote respective coordinates of the virtual illumination position in a spherical coordinate system, $\epsilon$ denotes a luminance attenuation constant, and $l(\varphi,\theta)$ denotes a luminance attenuation value which relates to the virtual illumination position.

9. The image processing method according to claim 8, wherein the luminance attenuation value $l(\varphi,\theta)$ is determined by applying Equation 1 below:

$$l(\phi, \theta) = 1 - Ae^{-\left(\frac{(\phi-\phi_0)^2}{2\sigma_\phi^2} + \frac{(\theta-\theta_0)^2}{2\sigma_\theta^2}\right)}$$ [Equation 1]

wherein $(\varphi,\theta)$ denotes respective coordinates of the virtual illumination position in a spherical coordinate system, $(\varphi_0,\theta_0)$ denotes respective coordinates of a reference position in the spherical coordinate system, $\sigma_\varphi$ and $\sigma_\theta$ denote respective values which relate to a distribution of a first virtual illumination position, and A denotes a predetermined constant.

10. The image processing method according to claim 1, wherein the correcting further comprises, when the virtual illumination position is represented by coordinates in a rectangular coordinate system, converting the coordinates which represent the virtual illumination position from the rectangular coordinate system into coordinates in a spherical coordinate system.

11. The image processing method according to claim 1, wherein the acquiring comprises acquiring shaded volume-rendered image data which relate to the object via volume rendering which is performed by using a shadow map in conjunction with virtual illumination.

12. An image processing apparatus comprising:
a volume data collector which is configured to collect volume data which relate to an object; and
an image processor configured to perform volume rendering of the collected volume data which relate to the object and to acquire rendered image data,
wherein the image processor is further configured to acquire information which relates to a virtual illumination position, to determine at least one conversion function from a plurality of conversion functions stored in a database based on the virtual illumination position which relates to the object, and to correct the acquired image data by using the virtual illumination position and the at least one conversion function, and
wherein the image processor is further configured to perform a tone mapping with respect to the acquired image data by using a second conversion function using a difference between coordinates of the virtual illumination position and coordinates of a reference position, and a distribution of the virtual illumination position.

13. The image processing apparatus according to claim 12, wherein the image processor is further configured to adjust a brightness of the acquired image data by using a first conversion function which is determined based on coordinates of the virtual illumination position.

14. The image processing apparatus according to claim 13, wherein the first conversion function includes an illumination attenuation function.

15. The image processing apparatus according to claim 13, wherein the image processor is further configured to perform a hue correction with respect to the acquired image data by using a third conversion function.

16. The image processing apparatus according to claim 13, wherein, when the virtual illumination position is represented by coordinates in a rectangular coordinate system, the image processor is further configured to convert the coordinates which represent the virtual illumination position from the rectangular coordinate system into coordinates in a spherical coordinate system.

17. The image processing apparatus according to claim 13, wherein the image processor is further configured to acquire volume-rendered image data which relate to the object by using a shadow map in conjunction with virtual illumination.

18. The image processing apparatus according to claim 13, wherein the image processor is further configured to acquire a projection image of the object which corresponds to at least one view point with respect to the acquired image data, and to correct the acquired projection image of the object based on the virtual illumination position by using the at least one conversion function.

* * * * *